United States Patent
Yamamura et al.

(10) Patent No.: US 10,697,883 B2
(45) Date of Patent: Jun. 30, 2020

(54) METHOD FOR DETERMINING APPLICATION OF THERAPY TO MULTIPLE SCLEROSIS (MS) PATIENT

(71) Applicants: National Center of Neurology and Psychiatry, Tokyo (JP); Chugai Seiyaku Kabushiki Kaisha, Tokyo (JP)

(72) Inventors: Takashi Yamamura, Tokyo (JP); Masakazu Nakamura, Tokyo (JP)

(73) Assignees: National Center of Neurology and Psychiatry, Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/575,027

(22) PCT Filed: May 19, 2016

(86) PCT No.: PCT/JP2016/064818
§ 371 (c)(1),
(2) Date: Nov. 17, 2017

(87) PCT Pub. No.: WO2016/186154
PCT Pub. Date: Nov. 24, 2016

(65) Prior Publication Data
US 2018/0149573 A1   May 31, 2018

(30) Foreign Application Priority Data

May 19, 2015 (JP) ................................ 2015-102142

(51) Int. Cl.
| | | |
|---|---|---|
| A61K 39/395 | (2006.01) | |
| G01N 33/53 | (2006.01) | |
| G01N 15/14 | (2006.01) | |
| G01N 33/48 | (2006.01) | |
| A61K 45/00 | (2006.01) | |
| A61P 25/00 | (2006.01) | |
| C07K 16/28 | (2006.01) | |
| G01N 15/00 | (2006.01) | |

(52) U.S. Cl.
CPC .......... *G01N 15/14* (2013.01); *A61K 39/395* (2013.01); *A61K 45/00* (2013.01); *A61P 25/00* (2018.01); *C07K 16/2866* (2013.01); *G01N 33/48* (2013.01); *G01N 2015/008* (2013.01); *G01N 2800/285* (2013.01); *G01N 2800/52* (2013.01)

(58) Field of Classification Search
CPC ................... A61K 2039/505; G01N 15/14
See application file for complete search history.

(56) References Cited

U.S. PATENT DOCUMENTS

| | | |
|---|---|---|
| 5,126,250 A | 6/1992 | McDonough et al. |
| 5,670,373 A | 9/1997 | Kishimoto |
| 5,817,790 A | 10/1998 | Tsuchiya et al. |
| 6,309,636 B1 | 10/2001 | Do Couto et al. |
| 6,723,319 B1 | 4/2004 | Ito et al. |
| 8,470,316 B2 | 6/2013 | Yasunami et al. |
| 8,562,991 B2 | 10/2013 | Igawa et al. |
| 8,623,355 B2 | 1/2014 | Okada et al. |
| 8,771,686 B2 | 7/2014 | Ishida et la. |
| 8,945,558 B2 | 2/2015 | Kobara et al. |
| 9,017,677 B2 | 4/2015 | Mihara |
| 9,260,516 B2 | 2/2016 | Nishimoto et al. |
| 9,539,322 B2 | 1/2017 | Nishimura et al. |
| 9,725,514 B2 | 8/2017 | Takahashi et al. |
| 2001/0001663 A1 | 5/2001 | Kishimoto et al. |
| 2002/0187150 A1 | 12/2002 | Mihara et al. |
| 2004/0018540 A1 | 1/2004 | Yamamura et al. |
| 2004/0071706 A1 | 4/2004 | Kishimoto et al. |
| 2005/0142635 A1 | 6/2005 | Tsuchiya et al. |
| 2005/0261229 A1 | 11/2005 | Gillies et al. |
| 2006/0292147 A1 | 12/2006 | Yoshizaki et al. |
| 2007/0036785 A1 | 2/2007 | Kishimoto et al. |
| 2007/0280945 A1 | 12/2007 | Stevens et al. |
| 2009/0291076 A1 | 11/2009 | Morichika et al. |
| 2010/0247523 A1 | 9/2010 | Kano et al. |
| 2010/0316636 A1 | 12/2010 | Radin et al. |
| 2011/0076275 A1 | 3/2011 | Igawa et al. |
| 2011/0098450 A1 | 4/2011 | Igawa et al. |

(Continued)

FOREIGN PATENT DOCUMENTS

| | | |
|---|---|---|
| AR | 068564 | 11/2009 |
| CA | 1 332 367 | 10/1994 |

(Continued)

OTHER PUBLICATIONS

U.S. Appl. No. 15/263,617, Igawa et al., filed Sep. 13, 2016.

(Continued)

*Primary Examiner* — Prema M Mertz
(74) *Attorney, Agent, or Firm* — Fish & Richardson P.C.

(57) ABSTRACT

According to the present invention, the therapeutic effect of an IL-6 inhibitor on MS was found to be predictable by using as indicators the amount of plasmablasts and/or the indicator of change in immature plasmablasts (amount of immature plasmablasts or amount of follicular helper T cells) in MS patients with a large amount of plasmablasts. Furthermore, IL-6 inhibitors were found to be effective against MS in which plasmablasts occur at high levels and in which the indicator of change in immature plasmablasts is high. The present invention provides methods for selecting MS cases for which treatment with an IL-6 inhibitor is effective, and also provides an effective therapeutic method for patients with MS in which plasmablast occur at high levels and in which the indicator of change in immature plasmablasts is high.

13 Claims, 3 Drawing Sheets

(56) References Cited

U.S. PATENT DOCUMENTS

| | | |
|---|---|---|
| 2011/0245473 A1 | 10/2011 | Igawa et al. |
| 2012/0253016 A1 | 10/2012 | Igawa et al. |
| 2012/0301460 A1 | 11/2012 | Bao et al. |
| 2013/0317203 A1 | 11/2013 | Igawa et al. |
| 2015/0166666 A1 | 6/2015 | Igawa et al. |
| 2016/0139117 A1 | 5/2016 | Yamamura et al. |
| 2017/0121412 A1 | 5/2017 | Igawa et al. |
| 2018/0148509 A1 | 5/2018 | Kakehi et al. |
| 2019/0085085 A1 | 3/2019 | Igawa et al. |

FOREIGN PATENT DOCUMENTS

| | | |
|---|---|---|
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 648 644 | 10/2007 |
| CA | 2 700 394 | 4/2009 |
| CA | 2 700 498 | 4/2009 |
| CN | 101849006 | 9/2010 |
| CN | 103476793 | 12/2013 |
| EP | 0 361 902 | 4/1990 |
| EP | 0 628 639 | 12/1994 |
| EP | 0 783 893 | 7/1997 |
| EP | 0 791 359 | 8/1997 |
| EP | 0 983 767 | 3/2000 |
| EP | 1 004 315 | 5/2000 |
| EP | 1 074 268 | 2/2001 |
| EP | 1 334 731 | 8/2003 |
| EP | 1 374 900 | 1/2004 |
| EP | 1 690 550 | 8/2006 |
| EP | 1 707 215 | 10/2006 |
| EP | 1 728 801 | 12/2006 |
| EP | 1 733 740 | 12/2006 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 990 060 | 11/2008 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 202 245 | 6/2010 |
| EP | 2 206 775 | 7/2010 |
| EP | 2 275 443 | 1/2011 |
| EP | 2 305 306 | 4/2011 |
| EP | 2 330 193 | 6/2011 |
| EP | 2 578 233 | 4/2013 |
| EP | 2 639 305 | 9/2013 |
| JP | H02-163096 | 6/1990 |
| JP | 2004/028926 | 1/2004 |
| JP | 2013/541594 | 11/2013 |
| KR | 2006/0010765 | 2/2006 |
| KR | 2007/0035482 | 3/2007 |
| RU | 2147442 | 4/2000 |
| RU | 2195960 | 1/2003 |
| RU | 2430111 | 9/2011 |
| TW | 2010/021829 | 6/2010 |
| WO | WO 92/19759 | 11/1992 |
| WO | WO 96/11020 | 4/1996 |
| WO | WO 96/12503 | 5/1996 |
| WO | WO 98/42377 | 10/1998 |
| WO | WO 99/08707 | 2/1999 |
| WO | WO 99/47170 | 9/1999 |
| WO | WO 99/58572 | 11/1999 |
| WO | WO 02/34292 | 5/2002 |
| WO | WO 02/080969 | 10/2002 |
| WO | WO 2004/096273 | 11/2004 |
| WO | WO 2005/037315 | 4/2005 |
| WO | WO 2005/061000 | 7/2005 |
| WO | WO 2005/080429 | 9/2005 |
| WO | WO 2005/090405 | 9/2005 |
| WO | WO 2006/023144 | 3/2006 |
| WO | WO 2006/070286 | 7/2006 |
| WO | WO 2006/119115 | 11/2006 |
| WO | WO 2007/043641 | 4/2007 |
| WO | WO 2007/046489 | 4/2007 |
| WO | WO 2007/058194 | 5/2007 |
| WO | WO 2007/061029 | 5/2007 |
| WO | WO 2007/074880 | 7/2007 |
| WO | WO 2007/086490 | 8/2007 |
| WO | WO 2007/114319 | 10/2007 |
| WO | WO 2007/137984 | 12/2007 |
| WO | WO 2007/143168 | 12/2007 |
| WO | WO 2008/020079 | 2/2008 |
| WO | WO 2008/090901 | 7/2008 |
| WO | WO 2009/010539 | 1/2009 |
| WO | WO 2009/014263 | 1/2009 |
| WO | WO 2009/041613 | 4/2009 |
| WO | WO 2009/041621 | 4/2009 |
| WO | WO 2009/041643 | 4/2009 |
| WO | WO 2009/044774 | 4/2009 |
| WO | WO 2009/125825 | 10/2009 |
| WO | WO 2009/148148 | 12/2009 |
| WO | WO 2010/035769 | 4/2010 |
| WO | WO 2010/065078 | 6/2010 |
| WO | WO 2010/107108 | 9/2010 |
| WO | WO 2011/149046 | 12/2011 |
| WO | WO 2012/063875 | 5/2012 |
| WO | WO 2012/064627 | 5/2012 |
| WO | WO 2012/118750 | 9/2012 |
| WO | WO 2014/200018 | 12/2014 |
| WO | WO 2016/136933 | 9/2016 |
| WO | WO 2018/203545 | 11/2018 |

OTHER PUBLICATIONS

U.S. Appl. No. 13/524,528, Igawa et al., filed Jun. 15, 2012.

U.S. Appl. No. 12/094,644, Nakashima et al., filed Feb. 27, 2009 (abandoned).

U.S. Appl. No. 12/996,162, Mitsunaga et al., filed Mar. 7, 2011.

U.S. Appl. No. 13/387,292, Maeda et al., filed Apr. 3, 2012.

Barkhof et al., "Comparison of MRI criteria at first presentation to predict conversion to clinically definite multiple sclerosis," Brain, Nov. 1997:120(Pt 11):2059-69.

Chihara et al., "Autoantibody producing cells in neuromyelitis optica," Journal of Clinical and Experimental Medicine, vol. 240:534-535, 2012 (with English translation).

Chihara et al., "Interleukin 6 signaling promotes anti-aquaporin 4 autoantibody production from plasmablasts in neuromyelitis optica," Proc. Natl. Acad. Sci. USA., Mar. 1, 2011;108(9):3701-6. doi:10.1073/pnas.1017385108. Epub Feb. 14, 2011.

Christensen et al., "Systemic Inflammation in Progressive Multiple Sclerosis Involves Follicular T-Helper, Th17- and Activated B-Cells and Correlates with Progression," PLoS One, 2013;8(3):e57820. doi:10.1371/journal.pone.0057820. Epub Mar. 1, 2013.

Cocco et al., "In Vitro Generation of Long-lived Human Plasma Cells," J. Immunol., Dec. 15, 2012;189(12):5773-85. doi:10.4049/jimmunol.1103720. Epub Nov. 16, 2012.

Houzen et al., "Increased prevalence, incidence, and female predominance of multiple sclerosis in northern Japan," J. Neurol. Sci., Dec. 15, 2012:323(1-2):117-22. doi:10.1016/j.jns.2012.08.032. Epub Sep. 17, 2012.

Jego et al., "Interleukin-6 is a growth factor for nonmalignant human plasmablasts," Blood, Mar. 15, 2001:97(6):1817-22.

Jourdan et al., "An in vitro model of differentiation of memory B cells into plasmablasts and plasma cells including detailed phenotypic and molecular characterization," Blood, Dec. 10, 2009:114(25):5173-81. doi:10.1182/blood-2009-07-235960.

Lucchinetti et al., "Heterogeneity of Multiple Sclerosis Lesions: Implications for the Pathogenesis of Demyelination," Ann. Neurol., Jun. 2000:47(6):707-17.

Matsumoto et al., "Interleukin-10-Producing Plasmablasts Exert Regulatory Function in Autoimmune Inflammation," Immunity, Dec. 18, 2014:41(6):1040-51. doi:10.1016/j.immuni.2014.10.016. Epub Nov. 4, 2014.

(56) References Cited

OTHER PUBLICATIONS

Miller et al., "Differential diagnosis of suspected multiple sclerosis: a consensus approach," Mult. Scler., Nov. 2008: 14(9):1157-74. doi:10.1177/1352458508096878. Epub Sep. 19, 2008.
Srivastava et al., "Potassium Channel IGR.4.1 as an Immune Target in Multiple Sclerosis," N. Engl. J. Med., Jul. 12, 2012:367(2):115-23. doi:10.1056/NEJMoa1110740.
Tintore et al., "Isolated Demyelinating Syndromes: Comparison of Different MR Imaging Criteria to Predict Conversion to Clinically Definite Multiple Sclerosis," AJNR Am. J. Neuroradiol., Apr. 2000:21(4):702-6.
International Search Report in International Application No. PCT/JP2016/064818, dated Aug. 16, 2016, 5 pages (with English translation).
International Preliminary Report on Patentability in International Application No. PCT/JP2016/064818, dated Nov. 30, 2017, 6 pages.
Abdalla et al., "Current Challenges of Cancer Anti-angiogenic Therapy and the Promise of Nanotherapeutics," Theranostics, Jan. 1, 2018, 8(2):533-548. doi: 10.7150/thno.21674. eCollection 2018.
Araki et al., "Emerging Disease-modifying Therapies for Neuromyelitis Optica Spectrum Disorder," The Medical Frontline, 2016, 71(6):1159-1167 (with English translation).
Hisanaga et al., "Neuro-Behcet disease and neuro-Sweet disease," Clinical Neurology, Dec. 31, 2011, 52:1234-1236 (with English abstract).
Ishikawa et al., "DNA microarray analysis of SLE related genes that respond to IL-6 blockade with tocilizumab, an anti-IL-6 receptor monoclonal antibody," Annals of the Rheumatic Diseases, 2006, 65(suppl 2):474.
Jacob et al., "Detrimental role of granulocyte-colony stimulating factor in neuromyelitis optica: clinical case and histological evidence," Mult Scler, Dec. 2012, 18(12):1801-1803. doi: 10.1177/1352458512443994. Epub Apr. 11, 2012.
Nishimoto et al., "Expressions of immune response related genes were normalised after tocilizumab treatment in rheumatoid arthritis (RA) patients," Annals of the Rheumatic Diseases,. 2013, 71(suppl 3):380.
Perez-Sanchez et al., "Diagnostic potential of NETosis-derived products for disease activity, atherosclerosis and therapeutic effectiveness in Rheumatoid Arthritis patients," J of Autoimmun, Aug. 2017, 82:31-40. doi: 10.1016/j.jaut.2017.04.007. Epub Apr. 29, 2017.
Ruiz-Limon et al., "Tocilizumab improves the proatherothrombotic profile of rheumatoid arthritis patients modulating endothelial dysfunction, NETosis, and inflammation," Transl Res, May 2017, 183:87-103. doi: 10.1016/j.trsl.2016.12.003. Epub Dec. 9, 2016.
Saadoun et al., "Neutrophil Protease Inhibition Reduces Neuromyelitis Optica-Immunoglobulin G-Induced Damage in Mouse Brain," Ann Neurol, Mar. 2012, 71(3):323-333. doi: 10.1002/ana.22686. Epub Feb. 28, 2012.
Sumida et al., "Anti-IL-6 receptor mAb eliminates myeloid-derived suppressor cells and inhibits tumor growth by enhancing T-cell responses," Eur J Immunol, Aug. 2012, 42(8):2060-72. doi: 10.1002/eji.201142335.
Tanaka et al., "Therapeutic Targeting of the Interleukin-6 Receptor," Annu Rev Pharmacol Toxicol, 2012, 52:199-219. doi: 10.1146/annurev-pharmtox-010611-134715. Epub Sep. 9, 2011.
Weber, "Why does cancer therapy lack effective anti-metastasis drugs," Cancer Lett, Jan. 28, 2013, 328(2):207-11. doi: 10.1016/j.canlet.2012.09.025. Epub Oct. 8, 2012.
Yamamura, "Anti-IL-6 receptor therapy for neuromyelitis optica," Neurological Therapeutics, Oct. 31, 2016, 33(5): S120 (with English translation).
Yamamura, "Anti-IL-6 receptor therapy for neuromyelitis optica," Presentation given at The 34th Annual Meeting of Japanese Society of Neurological Therapeutics, Nov. 4, 2016, 62 pages (with English translation).
Yamamura, "Treatment failures in NMO are due to specific immunologic mechanisms," Meeting of the 9th Annual International Roundtable Conference on NMO, Mar. 13, 2017, 21 pages.

U.S. Appl. No. 12/680,112, Igawa et al., filed Jun. 23, 2010 (abandoned).
U.S. Appl. No. 13/959,489, Igawa et al., filed Aug. 5, 2013 (abandoned).
U.S. Appl. No. 15/263,617, Igawa et al., filed Sep. 13, 2016 (abandoned).
U.S. Appl. No. 16/041,976, Igawa et al., filed Jul. 23, 2018.
U.S. Appl. No. 13/524,528, Igawa et al., filed Jun. 15, 2012 (abandoned).
U.S. Appl. No. 14/520,423, Igawa et al., filed Oct. 22, 2014.
U.S. Appl. No. 15/553,609, Kakehi et al., filed Aug. 25, 2017.
U.S. Appl. No. 14/897,498, Yamamura et al., filed Dec. 10, 2015.
U.S. Appl. No. 16/609,053, Matsuoka et al., filed Dec. 28, 2019.
Actemra (tocilizumab), Highlights of Prescribing Information, as revised in Aug. 2017 (1 page).
Akira et al., "Interleukin-6 in Biology and Medicine," Adv Immunol, 1993, vol. 54:1-78.
Ando et al., "Tocilizumab, a Proposed Therapy for the Cachexia of Interleukin6-Expressing Lung Cancer," Plos One, Jul. 10, 2014, 9(7):e102436. doi: 10.1371/journal.pone.0102436. eCollection 2014.
Annual Report 2012 (Integrated Edition including CSR Report), Chugai Pharmaceutical Co. Ltd., Mar. 27, 2013.
Araki et al., "Clinical Improvement in a Patient with Neuromyelitis Optica following Therapy with the Anti-IL-6 Receptor Monoclonal Antibody Tocilizumab," Mod Rheumatol, 2013, vol. 23:827-831.
Araki et al., "Efficacy of the anti-IL-6 receptor antibody tocilizumab in neuromyelitis optica," Neurology, Apr. 15, 2014, 82(15):1302-6. doi: 10.1212/WNL.0000000000000317. Epub Mar. 14, 2014.
Aricha et al., "Blocking of IL-6 Suppresses Experimental Autoimmune Myasthenia Gravis," J Autoimmun, Mar. 2011, vol. 36:135-141.
Armour et al., "Recombinant human IgG molecules lacking Fcγ receptor I binding and monocyte triggering activities," Eur J Immunol, Aug. 1999, 29(8):2613-24.
Balint et al., "Alterations of the peripheral B cell compartment in pediatric-onset multiple sclerosis," Journal of Neurology, May 2011, vol. 258, Suppl 1, p. S202, Abstract No. P732.
Bartelds et al., "Clinical response to adalimumab: relationship to anti-adalimumab antibodies and serum adalimumab concentrations in rheumatoid arthritis," Ann Rheum Dis, Jul. 2007, 66(7):921-6. Epub Feb. 14, 2007.
Bender et al., "Immunogenicity, efficacy and adverse events of adalimumab in RA patients," Rheumatol Int, Jan. 2007, 27(3):269-74. Epub Sep. 28, 2006.
Besada, "Potential patient benefit of a subcutaneous formulation of a tocilizumab for the treatment of rheumatoid arthritis: a critical review," Patient Preference and Adherence, Aug. 1, 20014, 8:1051-9. doi: 10.2147/PPA. S34958. eCollection 2014.
Brown et al., "Tolerance to Single, but Not Multiple, Amino Acid Replacements in Antibody $V_H$ CDR2," J Immunol, May 1, 1996, 156(9):3285-91.
Chau et al., "HuM291(NUVION), A Humanized Fc Receptor-Nonbinding; Antibody Against CD3, Anergizes Peripheral Blood T Cells as Partial Agonist of the T Cell Receptor," Transplantation, Apr. 15, 2001, 71(7):941-50.
Chien et al., "Significant structural and functional change of an antigen-binding site by a distant amino acid substitution: Proposal of a structural mechanism," Proc Natl Acad Sci USA. Jul. 1989, 86(14):5532-6.
Chirino et al., "Minimizing the immunogenicity of protein therapeutics," Drug Discov Today, Jan. 15, 2004, 9(2):82-90.
Choy, "Inhibiting Interleukin-6 in Rheumatoid Arthritis," Curr Rheumatol Rep, Oct. 2008, 10(5):413-7.
Chu et al., "Accumulation of Succinimide in a Recombinant Monoclonal Antibody in Mildly Acidic Buffers Under Elevated Temperatures," Pharm Res, Jun. 2007, 24(6):1145-56. Epub Mar. 24, 2007.
Chugai NMO Clinical Trial Webinar, Sakura Star Study, dated Dec. 12, 2014, downloaded on Sep. 5, 2019 from https://s3.amazonaws.com/gjcf-wp-uploads/wp-content/uploads/2016/05/16162202/12_12_14_Chugai_Webinar_PPT_Complete_Deck_FINAL.pdf, 18 pages.
Chugai Pharmaceutical, A phase I, multiple-dose study of SA237, Study JapicCTI-No. 121786; submitted to Clinicaltrials.jp on Jan.

(56) References Cited

OTHER PUBLICATIONS 31, 2014; downloaded from clinicaltrials.jp archive on Sep. 5, 2019 as https://www.clinicaltrials.jp/cti-user/trial/Show.jsp, 5 pages.

Chugai Pharmaceutical, A phase I, multiple-dose study of SA237, Study JapicCTI-No. 121786; submitted to Clinicaltrials.jp on Jun. 19, 2012; downloaded from clinicaltrials.jp archive on Sep. 5, 2019 as https://www.clinicaltrials.jp/cti-user/trial/Show.jsp, 5 pages.

Chugai Pharmaceutical, A phase I, multiple-dose study of SA237, Study JapicCTI-No. 121786; submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V_3=View#StudyPageTop, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT02028884?V_4=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT02073279?V_1=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V_2=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT02073279?V_3=View#StudyPageTop, 7 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V_7=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V_12=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.

Cole et al., "Human IgG2 Variants of Chimeric Anti-CD3 Are Nonmitogenic to T Cells," J. Immunol, Oct. 1, 1997, 159(7):3613-21.

Cordoba et al., "Non-enzymatic hinge region fragmentation of antibodies in solution," J Chromatogr B Analyt Technol Biomed Life Sci, Apr. 25, 2005, 818(2):115-21.

(56) References Cited

OTHER PUBLICATIONS

Costa et al., "Efficacy of tocilizumab in a patient with refractory psoriatic arthritis," Clin Rheumatol, Sep. 2014, 33(9):1355-7. doi: 10.1007/s10067-014-2603-5. Epub Apr. 8, 2014.
Damschroder et al., "Framework shuffling of antibodies to reduce immunogenicity and manipulate functional and biophysical properties," Mol Immunol, Apr. 2007, 44(11):3049-60. Epub Jan. 22, 2007.
Davies et al., "Affinity improvement of single antibody VH domains: residues in all three hypervariable regions affect antigen binding," Immunotechnology, Sep. 1996, 2(3):169-79.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, Sep. 15, 2002, 169(6):3076-84.
Dillon et al., "Structural and Functional Characterization of Disulfide Isoforms of the Human IgG2 Subclass," J Biol Chem, Jun. 6, 2008, 283(23):16206-15. Epub Mar. 12, 2008.
Ewert et al., "Stability improvement of antibodies for extracellular and intracellular applications: CDR grafting to stable frameworks and structure-based framework engineering," Methods, Oct. 2004, 34(2):184-99.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-search/trial/2013-003752-21/DE, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctr-search/trial/2013-003752-21/HU, 6 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search/trial/2013-003752-21/IT, 5 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/GB, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search/trial/2015-005431-41/CR, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.
Furuya et al., "Interleukin-6 as a Potential Therapeutic Target for Pulmonary Arterial Hypertension," Int J Rheumatol, Aug. 2010, 2010:720305. doi: 10.1155/2010/720305. Epub Aug. 2, 2010.
Gessner et al., "The IgG receptor family," Ann Hematol, Jun. 1998, 76(6):231-48.
Ghetie et al., "Increasing the serum persistence of an IgG fragment by random mutagenesis," Nat Biotechnol, Jul. 1997, 15(7):637-40.
Guerne et al., "Synovium as a Source of Interleukin 6 in Vitro—Contribution to Local and Systemic Manifestations of Arthritis," J Clin Invest, Feb. 1989, 83(2):585-92.
Guyre et al., "Increased potency of Fc-receptor-targeted antigens," Cancer Immunol Immunother, Nov.-Dec. 1997, 45(3-4):146-8.
Hanes et al., "Picomolar affinity antibodies from a fully synthetic naïve library selected and evolved by ribosome display," Nat Biotechnol, Dec. 2000, 18(12):1287-92.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-23. doi: 10.1007/s00296-009-1075-4. Epub Jul. 29, 2009.
Hinton et al., "An Engineered Human IgG1 Antibody with Longer Serum Half-Life," J Immunol, Jan. 1, 2006, 176(1):346-56.
Hirano et al., "Excessive production of interleukin 6/B cell stimulatory factor-2 in rheumatoid arthritis," Eur J Immunol, Nov. 1988, 18(11):1797-801.
Hirano et al., "Complementary DNA for a Novel Human Interleukin (BSF-2) that Induces B. Lymphocytes to Produce Immunoglobulin," Nature, Nov. 1986, vol. 324:73-76.
Hirata et al., "Characterization of IL-6 Receptor Expression by Monoclonal and Polyclonal Antibodies," J Immunol, Nov. 1, 1989, vol. 143:2900-2906.
Holt et al., "Domain antibodies: proteins for therapy," Trends Biotechnol, Nov. 2003, 21(11):484-90.
Honda et al., "Marginal zone B cells exacerbate endotoxic shock via interleukin-6 secretion induced by Fcα/μR-coupled TLR4 signalling," Nat Commun, May 5, 2016, 7:11498. doi: 10.1038/ncomms11498.
Hosokawa et al., "Evaluation of Interferon-β1bTreatment for Multiple Sclerosis," Shinkei Chiryo, 2008, vol. 25:589-595 (with English translation).
Houssiau et al., "Interleukin-6 in Synovial Fluid and Serum of Patients with Rheumatoid Arthritis and Other Inflammatory Arthritides," Arthritis Rheum, Jun. 1988, 31(6):784-8.
Huang et al., "A Monoclonal Anti-Human IL-6 Receptor Antibody Inhibits the Proliferation of Human Myeloma Cells," Hybridoma, Oct. 1993, vol. 12:621-630.
Huizinga et al., "Sarilumab, a fully human monoclonal antibody against IL-6Rα in patients with.rheumatoid arthritis and an inadequate response to methotrexate: efficacy and safety results from the randomised SARIL-RA-Mobility Part A trial," Ann Rheum Dis, Sep. 2014, 73(9):1626-34. doi: 10. 1136/annrheumdis-2013-204405. Epub Dec. 2, 2013.

(56) References Cited

OTHER PUBLICATIONS

Hwang et al., "Use of human germline genes in a CDR homology-based approach to antibody humanization," Methods, May 2005, 36(1):35-42.
Iijima et al., "Tocilizumab improves systemic rheumatoid vasculitis with necrotizing crescentic glomerulonephritis," Mod Rheumatol, Jan. 2015, 25(1):138-42. doi: 10.3109/14397595.2013.874748. Epub Feb. 18, 2014.
Interleukin 6, Wikipedia, Feb. 22, 2019, XP055598802, (URL:https://protect-us.mimecast.com/s/6UxpCmZ28nsAp18JuGhTki?domain=en.wikipedia.org), retrieved on Jun. 24, 2019, 20 pages.
Ito et al., "The His-probe method: effects of histidine residues introduced into the complementarity-determining regions of antibodies on antigen-antibody interactions at different pH values," FEBS Lett, Aug. 31, 1992, 309(1):85-8.
Japanese Society of Neurological Therapeutics, "Standard Neurological Therapeutics: Neuromyelitis Optica (NMO)," 2013, vol. 30, No. 6, pp. 777-794 (with English translation of relevant passages).
Johnson et al., "Cation exchange-HPLC and mass spectrometry reveal C-terminal amidation of an IgG1 heavy chain," Anal Biochem, Jan. 1, 2007, 360(1):75-83. Epub Oct. 30, 2006.
Jones et al., "Identification and removal of a promiscuous CD4+ T cell epitope from the C1 domain of factor VIII," J Thromb Haemost, May 2005, 3(5):991-1000.
Kakuron, "Section 9 Opticospinal Multiple Sclerosis," Tahatsusei Kokasho Chiryo Guideline, 2010, vol. 2010, pp. 104-109 (with English translation).
Kim et al., "Antibody engineering for the development of therapeutic antibodies," Mol Cells, Aug. 31, 2005, 20(1):17-29.
Kishimoto, "Interleukin-6 and its a:123-32 Receptor in Autoimmunity," J Autoimmun, Apr. 5, 1992 Suppl A:123-32.
Kishimoto, "The Biology of Interleukin-6," Blood, Jul. 1989, 74(10):1-10.
Kondo et al., "A case of overlap syndrome successfully treated with tocilizumab: a hopeful treatment strategy for refractory dermatomyositis?," Rheumatology, Oct. 2014, 53(10):1907-8. doi: 10.1093/rheumatology/keu234. Epub May 23, 2014.
Kotake et al., "Interleukin-6 and Soluble Interleukin-6 Receptors in the Synovial Fluids from Rheumatoid Arthritis Patients Are Responsible for Osteoclast-like Cell Formation," J Bone Miner Res, Jan. 1996, 11(1):88-95.
Krieckaert et al., "Immunogenicity of Biologic Therapies—We Need Tolerance," Nat Rev Rheumatol, Oct. 2010, vol. 6:558-559. doi: 10.1038/nrrheum.2010.153.
Lotz et al., "B Cell Stimulating Factor 2/Interleukin 6 is a Costimulant for Human Thymocytes and T Lymphocytes," J Exp Med, Mar. 1988, vol. 167:1253-1258.
Maccallum et al., "Antibody-antigen Interactions: Contact Analysis and Binding Site Topography," J Mol Biol, Oct. 11, 1996, 262(5):732-45.
Madhok et al., "Serum interleukin 6 levels in rheumatoid arthritis: correlations with clinical and laboratory indices of disease activity," Ann Rheum Dis, Mar. 1993, 52(3):232-4.
Maini et al., "Double-Blind Randomized Controlled Clinical Trial of the Interleukin-6 Receptor Antagonist, Tocilizumab, in European Patients With Rheumatoid Arthritis Who Had an Incomplete Response to Methotrexate," Arthritis Rheum, Sep. 2006, 54(9):2817-29.
Maynard et al., "Antibody Engineering," Annu Rev Biomed Eng, Aug. 2000, 2:339-76.
Mihara et al., "Tocilizumab inhibits signal transduction mediated by both mIL-6R and sIL-6R, but not by the receptors of other members of IL-6 cytokine family," Int Immunopharmacol, Nov. 2005, 5(12):1731-40.
Mihara et al., "Anti-Interleukin 6 Receptor Antibody Inhibits Murine AA-Amyloidosis," J Rheumatol, Jun. 2004, 31(6):1132-8
Mori et al., "Novel models of cancer-related anemia in mice inoculated with IL-6-producing tumor cells," Biomed Res, Feb. 2009, 30(1):47-51.

Motozawa et al., "Unique circumferential peripheral keratitis in relapsing polychondritis," Medicine, Oct. 2017, 96(41):e7951. doi: 10.1097/MD.0000000000007951.
Nakamura et al., "Clinical Features of Multiple Sclerosis with High Plasmablast Frequency in Peripheral Blood," Keystone Symposia on Molecular and Cellular Biology, Jan. 11, 2013, 3 pages.
Nakamura et al., "Clinical Features of Multiple Sclerosis with High Plasmablast Frequency in Peripheral Blood," Keystone Symposia on Molecular and Cellular Biology, Dec. 11, 2012, 1 page.
Nakamura et al., "Clinical Features of Multiple Sclerosis with High Plasmablast Frequency in Peripheral Blood," Keystone Symposia on Molecular and Cellular Biology, Jan. 14, 2013, 2 pages.
Nakamura et al., "Clinical Characteristics of Multiple Sclerosis with High Peripheral Blood Plasmablast Frequency," 54th Annual Meeting of the Japanese Society of Neurology, Apr. 30, 2013, 3 pages (with English translation).
Nakamura et al., "Clinical Features of Multiple Sclerosis with High Plasmablast Frequency in Peripheral Blood," 54th Annual Meeting of the Japanese Society of Neurology, Jun. 1, 2013, 3 pages.
Nakamura et al., "IL-6-dependent Plasmablasts in Pathological Conditions of Relapsing-Remitting Multiple Sclerosis," J Clin Immunol, 2013, vol. 36:345, W5-5 (with English translation).
Nakamura et al., "Plasmablast in the Pathology of Multiple Sclerosis," Jpn J Clin Immunol, 2015, 38(5):403-411 (with English summary).
Narazaki et al., "Therapeutic effect of tocilizumab on two patients with polymyositis," Rheumatology, Jul. 2011, 50(7):1344-6. doi: 10.1093/rheumatology/ker152. Epub Apr. 22, 2011.
Nishimoto et al., "Clinical Studies in Patients with Castleman's Disease, Crohn's Disease, and Rheumatoid Arthritis in Japan," Clin Rev Allergy Immunol, Jun. 2005, 28(3):221-30.
Nishimoto et al., "Interleukin 6: from bench to bedside," Nat Clin Pract Rheumatol, Nov. 2006, 2(11):619-26.
Nishimoto et al., "Humanized Anti-Interleukin-6 Receptor Antibody Treatment of Multicentric Castleman Disease," Blood, Oct. 15, 2005, vol. 106:2627-2632.
Novick et al., "Monoclonal Antibodies to the Soluble Human IL-6 Receptor: Affinity Purification, ELISA, and Inhibition of Ligand Binding," Hybridoma, Feb. 1991, vol. 10:137-146.
Ohno et al., Antigen-binding specificities of antibodies are primarily determined by seven residues of $V_H$, Proc Natl Acad Sci USA, May 1985, 82(9):2945-9.
Ohsugi, "Current Antibody Drugs—Developments/Manufacturing Technology/Scope of Patents," Pharm stage, 2007, 7(5):13-8 (with English translation).
Okabe, Proprietary Innovative Antibody Engineering Technologies in Chugai Pharmaceutical, Information Meeting on Antibody Engineering Technologies, Dec. 18, 2012.
Okiyama et al., "Therapeutic Effects of Interleukin-6 Blockade in a Murine Model of Polymyositis That Does Not Require Interleukin-17A," Arthritis Rheum, Aug. 2009, 60(8):2505-12.
Onda et al., "Lowering the Isoelectric Point of the Fv Portion of Recombinant Immunotoxins Leads to Decreased Nonspecific Animal Toxicity without Affecting Antitumor Activity," Cancer Res, Jul. 1, 2001, 61(13):5070-7.
Padlan et al., "Structure of an antibody-antigen complex: Crystal structure of the HyHEL-10 Fab-lysozyme complex," Proc Natl Acad Sci USA, Aug. 1989, 86(15):5938-42.
Pavlou et al., "The therapeutic antibodies market to 2008," Eur J Pharm Biopharm, Apr. 2005, 59(3):389-96.
Pini et al., "Design and Use of a Phage Display Library—Human Antibodies with Subnanomolar Affinity Against a Marker of Angiogenesis Eluted from a Two-Dimensional Gel," J Biol Chem, Aug. 21, 1998, 273(34):21769-76.
Polman et al., "Diagnostic Criteria for Multiple Sclerosis: 2010 Revisions to the McDonald Criteria," Ann Neurol, Jan. 11, 2011, 69:292-302.
Rajpal et al., "A general method for greatly improving the affinity of antibodies by using combinatorial libraries," Proc Natl Acad Sci USA, Jun. 14, 2005, 102(24):8466-71. Epub Jun. 6, 2005.
Reddy et al., "Elimination of Fc Receptor-Dependent Effector Functions of a Modified IgG4 Monoclonal Antibody to Human CD4," J Immunol, Feb. 15, 2000, 164(4):1925-33.

(56) References Cited

OTHER PUBLICATIONS

Reichert, "Antibodies to Watch in 2014," mAbs, Jul.-Aug. 2014, vol. 6:799-802. doi: 10.4161/mabs.29282. Epub May 19, 2014.
Reichert et al., "Monoclonal antibody successes in the clinic," Nat Biotechnol, Sep. 2005, 23(9):1073-8.
Roitt et al., Immunology, M., Mir, 2000, p. 110 (with English translation).
Rothe et al., "Ribosome Display for Improved Biotherapeutic Molecules," Expert Opin Biol Ther, Feb. 2006, 6(2):177-87.
Rudikoff et al., "Single amino acid substitution altering antigen-binding specificity," Proc Natl Acad Sci USA, Mar. 1982, 79(6):1979-83.
Sack et al., "Interleukin-6 in synovial fluid is closely associated with chronic synovitis in rheumatoid arthritis," Rheumatol Int, Jun. 1993, 13(2):45-51.
Salfeld, "Isotype selection in antibody engineering," Nat Biotechnol, Dec. 2007, 25(12):1369-72.
Sato et al., "Reshaping a Human Antibody to Inhibit the Interleukin 6-dependent Tumor Cell Growth," Cancer Res, Feb. 15, 1993, 53(4):851-6.
Sebba et al., "Tocilizumab: The first interleukin-6-receptor inhibitor," Am J Health Syst Pharm, Aug. 1, 2008, 65(15):1413-8. doi: 10.2146/ajhp070449.
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-6. doi: 10.1073/pnas.0802218105. Epub Jun. 24, 2008.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-9. doi: 10.1007/s10165-011-0416-9. Epub Feb. 9, 2011.
Shimizu et al., "IFNβ-1b May Severely Exacerbate Japanese Optic-Spinal MS in Neuromyelitis Optica Spectrum," Neurology, Sep. 8, 2010, vol. 75:1423-1427.
Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.
Shire et al., "Challenges in the Development of High Protein Concentration Formulations," J Pharm Sci, Jun. 2004, 93(6):1390-402.
Silpa-Archa et al., "Outcome of tocilizumab treatment in refractory ocular inflammatory diseases," Acta Ophthalmol, Sep. 2016, 94(6):e400-6. doi: 10.1111/aos.13015. Epub Mar. 24, 2016.
Strand et al., "Biologic therapies in rheumatology: lessons learned, future directions," Nat Rev Drug Discov, Jan. 2007, 6(1):75-92.
Suzuki et al., "Anti-murine IL-6 receptor antibody inhibits IL-6 effects in vivo," Immunol Lett, Sep. 1991, 30(1):17-21.
Taga et al., "Receptors for B Cell Stimulatory Factor 2," J Exp Med, Oct. 1, 1987, vol. 166: 967-981.
Taga et al., "Interleukin-6 Triggers the Association of its Receptor with a Possible Signal Transducer, gp130," Cell, Aug. 11, 1989, vol. 58:573-581.
Takkinen et al., Chapter 8 "Affinity and Specificity Maturation by CDR Walking," Antibody Engineering, Springer Lab Manuals, 2001, pp. 540-545.
Tamura et al., "Soluble interleukin-6 receptor triggers osteoclast formation by interleukin 6," Proc Natl Acad Sci USA, Dec. 15, 1993, 90(24):11924-8.
Tan et al., "Engineering the isoelectric point of a renal cell carcinoma targeting antibody greatly enhances scFv solubility," Immunotechnology, Oct. 1998, 4(2):107-14.
Teeling et al., "The Biological Activity of Human CD20 Monoclonal Antibodies Is Linked to Unique Epitopes on CD20," J Immunol, Jul. 1, 2006, 177(1):362-71.
Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-28.
Van Walle et al., "Immunogenicity screening in protein drug development," Expert Opin Biol Ther, Mar. 2007, 7(3):405-18.
Waubant et al., "Clinical Characteristics of Responders to Interferon Therapy for Relapsing MS," Neurology, Jul. 21, 2003, vol. 61:184-189.
Wingerchuk et al., "Revised diagnostic criteria for neuromyelitis optica," Neurology, May 22, 2006, 66:1485-1489.
Wingerchuk et al., "International consensus diagnostic criteria for neuromyelitis optica spectrum disorders," Neurology, Jul. 14, 2015, 85:177-189.
Wu et al., "Humanization of a Murine Monoclonal Antibody by Simultaneous Optimization of Framework and CDR Residues," J Mol Biol, Nov. 19, 1999, 294(1):151-62.
Wu et al., "Development of Motovizumab, an Ultra-potent Antibody for the Prevention of Respiratory Syncytial Virus Infection in the Upper and Lower Respiratory Tract," J Mol Biol, May 4, 2007, 368(3):652-65. Epub Feb. 20, 2007.
Yamasaki et al., "Cloning and Expression of the Human Interleukin-6 (BSF-2/IFNβ) Receptor," Science, Aug. 12, 1988, vol. 241:825-828
Yokota et al., "Clinical Study of Tocilizumab in Children With Systemic Onset-Juvenile Idiopathic Arthritis," Clin Rev Allergy Immunol, Jun. 2005, 28(3):231-8.
USPTO Restriction Requirement in U.S. Appl. No. 14/897,498, dated Dec. 18, 2017, 7 pages.
USPTO Non-Final Office Action in U.S. Appl. No. 14/897,498, dated Jun. 22, 2018, 16 pages.
USPTO Final Office Action in U.S. Appl. No. 14/897,498, dated Jan. 30, 2019, 15 pages.
USPTO Non-Final Office Action in U.S. Appl. No. 14/897,498, dated Aug. 21, 2019, 10 pages.

METHOD FOR DETERMINING APPLICATION OF THERAPY TO MULTIPLE SCLEROSIS (MS) PATIENT

CROSS-REFERENCE TO RELATED APPLICATIONS

This application is the National Stage of International Application Serial No. PCT/JP2016/064818, filed on May 19, 2016, which claims the benefit of Japanese Application Serial No. 2015-102142, filed on May 19, 2015.

TECHNICAL FIELD

The present invention relates to methods for predicting the therapeutic effect of an IL-6 inhibitor on a multiple sclerosis (MS) patient by using an "immature plasmablast (PB) indicator". The present invention also relates to agents for treating multiple sclerosis comprising an IL-6 inhibitor; and particularly to agents for treating multiple sclerosis in which plasmablasts occur at high levels and in which an indicator of change in immature plasmablasts is high.

BACKGROUND ART

Multiple sclerosis (MS) is considered as an autoimmune disease of the central nervous system. This disease manifests diverse neurological symptoms such as motor paralysis, sensory impairment, higher brain dysfunction, visual loss, and dysuria due to infiltration of autoreactive lymphocytes (mainly, T cells or B cells) into the brain, the spinal cord, or the optic nerve, causing inflammations targeting perineural myelin proteins. Approximately a million people are presumed to suffer from this disease worldwide. Particularly, in Western countries, MS is highly prevalent and is known as a typical neurological disease for young adults. Although the disease had been thought to be less common in Asian countries, abrupt increase in its prevalence has been reported in Japan in recent years (Non Patent Literature 1). This strongly suggests the involvement of not only genetic factors but environmental factors in the occurrence of MS, and is also presenting problems in that neurological symptoms remaining as sequelae result in breakdown of family life and social life including occupations. The great majority of MS patients develop transient and repetitive inflammations at various sites of the central nervous system. As each inflammation occurs, neurological symptoms are manifested depending on the inflammation site. This clinical event is called "relapse", and the course of recurrence is referred to as "relapsing-remitting (RR)". In relapsing-remitting MS (RRMS), sequelae accumulate with each relapse, leading to increasing deterioration of the activities of daily living (ADL). When the affected period becomes longer, more cases move on to secondary progressive (SP) MS, in which neurological symptoms gradually progress without relapses. At this stage, the great majority of cases already have moderate fixed neurological disability. Thus, treatment from an earlier stage, i.e. the RRMS stage, is believed to be important.

Recombinant interferon beta (IFN-β) has been used as the first line therapy to prevent relapses of RRMS, and is reported to be effective for suppressing the relapses and also effective for suppressing progression in the degree of impairment. In Japan, Avonex (registered trademark) (interferon beta-1a) and Betaferon (registered trademark) (interferon beta-1b) are used. However, their administration becomes difficult to continue in many patients due to manifestation of serious adverse reactions (interstitial pneumonia, autoimmune hepatitis, thyroid dysfunction, skin ulcer, psychological symptoms such as depression, leukopenia, etc.), or due to aggravation of latent immune disorders (collagen disease, thyroiditis, etc.) the patients may have originating from autoimmune abnormalities. Also, it has been reported that 30 to 50% of the patient population who may continue administration are resistant cases which show no therapeutic effect or result in aggravation of symptoms. These facts imply that RRMS includes a subgroup where administration of IFN-β should be avoided, while it is difficult to predict patients to whom IFN-β is not applicable (IFN-β-nonresponsive patients) before administration of IFN-β.

For patients to whom IFN-β is not applicable, the process of assessing whether IFN-β is applicable accompanies great suffering. Specifically, in cases where administration is discontinued due to serious adverse reaction or aggravation of concomitant immune disorder, the fact that IFN-β is not applicable is not known until administration of IFN-β is attempted and these events manifest. Even when administration can be continued, a length of treatment of at least half a year to 1 year is required for determining its therapeutic effect. Since the mode of administration of IFN-β preparations is self-injection (intramuscular injection or subcutaneous injection), this administration is painful and, in addition, the patients must endure adverse reactions such as influenza-like symptoms and headaches, which, while not leading to discontinuation of the administration, require some additional treatments.

Thus, there has been a strong demand for development of a method for predicting the therapeutic effect of IFN-β, the manifestation of a serious adverse reaction, and the aggravation of concomitant immune disorder before the start of treatment in order to avoid painful, unnecessary medication for patients to whom IFN-β is not applicable and to appropriately select applicable patients. In addition, the patients to whom IFN-β is not applicable are often difficult to treat even with other drugs. Thus, it has also been required to establish a novel treatment method.

Previously, a method which involves measuring the expression level of a particular gene group in leukocytes derived from the peripheral blood of a patient by use of a DNA chip or the like has been reported as a method for predicting the therapeutic effect of IFN-β on RRMS (Patent Literature 1).

Plasmablasts (PBs) are a subset of B cells, a type of lymphocytes, and have the specialized function of producing antibodies. In neuromyelitis optica (NMO), an autoimmune disease of the central nervous system the distinction of which from MS is clinically important despite its pathology different from MS, PBs have been identified as a source of production of anti-aquaporin 4 antibody (anti-AQP4 antibody), which is an autoantibody deeply involved in the pathogenesis of NMO, and have been reported to be increased in the peripheral blood of NMO patients (Non Patent Literature 2). The survival of NMO patient-derived PBs and their ability to produce the anti-AQP4 antibody are also known to be promoted in a manner dependent on interleukin 6 (IL-6) (Non Patent Literature 2). It has been reported so far that typical RRMS patients have a peripheral blood PB frequency equivalent to that of healthy persons (Non Patent Literature 2), and that SPMS patients show an increase of PBs in the peripheral blood (Non Patent Literature 3). A previous pathological study of MS brain lesions has suggested the involvement of an autoantibody in the formation of the lesions (Non Patent Literature 4). Recently, the presence of a disease-specific autoantibody in the serum of MS (including RRMS) patients has been reported (Non Patent Literature 5).

Furthermore, it has been reported that the therapeutic effect of an IL-6 inhibitor is high on patients with RRMS in which PBs occur at high levels, and that the therapeutic effect of an IL-6 inhibitor on RRMS can be predicted using the amount of PBs derived from RRMS patients as an indicator (Patent Literature 2). However, further establishment of a highly accurate and effective prediction method is desired.

PRIOR ART LITERATURES

Patent Literature

Patent Literature 1: Japanese Patent Application Kokai Publication No. (JP-A) 2004-28926 (unexamined, published Japanese patent application)
Patent Literature 2: WO2014/200018

Non Patent Literature

Non Patent Literature 1: J Neurol Sci 2012; 323 (1-2): 117-122
Non Patent Literature 2: Proc Natl Acad Sci USA 2011; 108(9): 3701-3706
Non Patent Literature 3: Plos One 2013; 8(3): e57820
Non Patent Literature 4: Ann Neurol 2000; 47(6): 707-717
Non Patent Literature 5: N Engl J Med 2012; 367(2): 115-123
Non Patent Literature 6: Mult Scler 2008; 14: 1157-1174
Non Patent Literature 7: Brain 1997; 120: 2059-2069
Non Patent Literature 8: Am J Neuroradiol 2000; 21: 702-706

SUMMARY OF THE INVENTION

Problems to be Solved by the Invention

The present invention was achieved in view of the above circumstances. An objective of the present invention is to provide a method for predicting the therapeutic effect of an IL-6 inhibitor on MS, by using an MS patient's peripheral blood immature plasmablast indicator. A further objective of the present invention is to identify MS patients to whom an IL-6 inhibitor can be applied, and to provide a therapeutic agent to be administered to such a patient.

Means for Solving the Problems

The present inventors performed dedicated research to solve the above-mentioned problems. First, the present inventors examined RRMS patients having a high amount of plasmablasts for the amount of follicular helper T cells. As a result, the RRMS patients having a high amount of plasmablasts were found to include a group of patients in which the amount of follicular helper T cells was small.

Next, the present inventors administered the IL-6 inhibitor tocilizumab to RRMS patients having a high amount of plasmablasts. The results led to the finding that among the RRMS patients having a high amount of plasmablasts, the efficacy of tocilizumab was high in patients carrying a small amount of follicular helper T cells, but low in patients carrying a large amount of follicular helper T cells. Furthermore, the present inventors elucidated that in patients for which the efficacy of tocilizumab is low, differentiation of B cells into immature PBs was mild, and the amount of immature PBs in the peripheral blood showed a small increase when it was compared between before and after the tocilizumab administration, and that in contrast, in patients for which the efficacy of tocilizumab is high, the amount of immature PBs in the peripheral blood showed a large increase when it was compared between before and after the administration.

The present invention is based on these findings, and specifically includes the following:
[1] Use of an immature plasmablast indicator in determining the therapeutic effect of an IL-6 inhibitor on multiple sclerosis.
[2] A method for predicting the therapeutic effect of an IL-6 inhibitor on a multiple sclerosis patient, which comprises the steps of:
  (i) measuring the amount of plasmablasts and/or an indicator of change in immature plasmablasts contained in a biological sample isolated from a multiple sclerosis patient; and
  (ii) predicting that the therapeutic effect of the IL-6 inhibitor is high when the indicator of change in immature plasmablasts is determined to be high in a group of high-plasmablast-level patients having a high amount of plasmablasts as compared with a healthy individual.
[3] The method of [1] or [2], wherein the amount of plasmablasts is determined to be high when the proportion of the plasmablasts to $CD19^+$ B cells is 3.50% or more.
[4] The method of any one of [1] to [3], wherein the indicator of change in immature plasmablasts is measured as an indicator of the amount of follicular helper T cells.
[5] The method of any one of [1] to [4], wherein the amount of follicular helper T cells is determined by a proportion of CXCR5+CCR7+ cells in memory CD4+ T cells, and the indicator of change in immature plasmablasts is indicated to be high when said proportion is low.
[6] The method of [5], wherein when the proportion of CXCR5+CCR7+ cells in memory CD4+ T cells is lower than 30%, the indicator of change in an immature plasmablast is determined to be high.
[7] The method of [5], wherein when the proportion of CXCR5+CCR7+ cells in memory CD4+ T cells is lower than 28.2%, the indicator of change in immature plasmablasts is determined to be high.
[8] The method of any one of [1] to [7], wherein the IL-6 inhibitor is an anti-IL-6 receptor antibody.
[9] The method of [8], wherein the anti-IL-6 receptor antibody is a chimeric antibody, a humanized antibody, or a human antibody.
[10] The method of any one of [1] to [9], wherein the multiple sclerosis is relapsing-remitting multiple sclerosis or secondary-progressive multiple sclerosis.
[11] An agent for treating multiple sclerosis in which plasmablasts occur at high levels and in which an indicator of change in immature plasmablasts is high, the agent comprising an IL-6 inhibitor as an active ingredient.
[12] The therapeutic agent of [11], wherein the IL-6 inhibitor is an anti-IL-6 receptor antibody.
[13] The therapeutic agent of [12], wherein the anti-IL-6 receptor antibody is a chimeric antibody, a humanized antibody, or a human antibody.
[14] The therapeutic agent of any one of [11] to [13], wherein the multiple sclerosis is relapsing-remitting multiple sclerosis or secondary-progressive multiple sclerosis.

Effects of the Invention

The present invention provides a method for predicting the therapeutic effect of an IL-6 inhibitor on MS by using an immature plasmablast indicator of an MS patient. By the method of the present invention, it is possible to avoid administering an IL-6 inhibitor to a patient who cannot be expected to receive the therapeutic effect of an IL-6 inhibitor or who has to suffer manifestation of serious adverse reactions or aggravation of concomitant immune disorders, and it is possible to select a suitable treatment method. Furthermore, the present invention led to the finding that an IL-6 inhibitor is effective for treating patients with MS in which plasmablasts occur at high levels and in which an indicator of change in immature plasmablasts is high. Accordingly, the present invention provides a therapeutic agent for MS in which plasmablasts occur at high levels and in which an indicator of change in immature plasmablasts is high.

MODE FOR CARRYING OUT THE INVENTION

Figure 1:
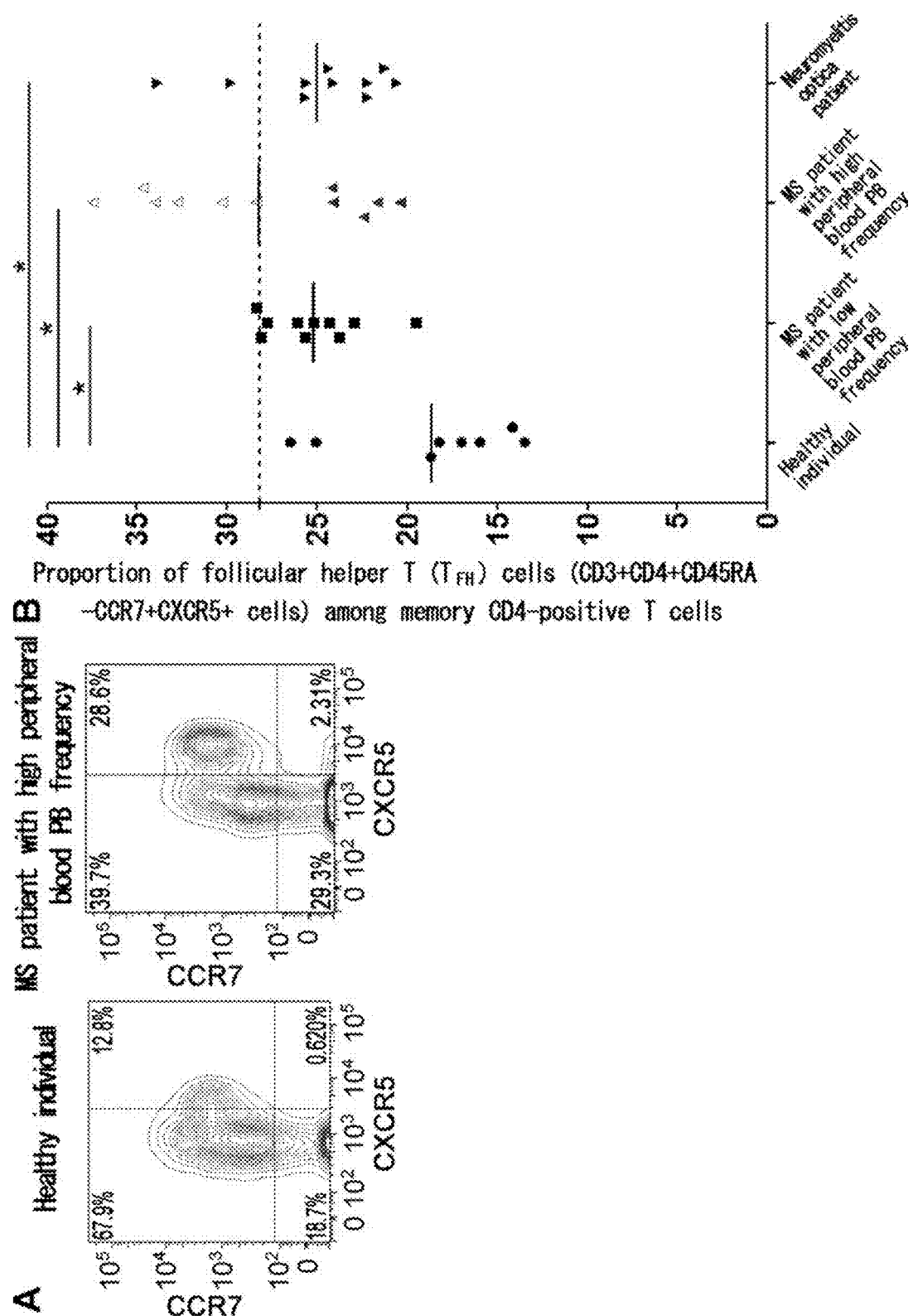
FIG. 1 shows increase in peripheral blood follicular helper T ($T_{FH}$) cells in RRMS patients having a high peripheral blood PB frequency. Using peripheral blood mononuclear cells (PBMC) derived from healthy individuals (HD; n=8), MS patients with a low peripheral blood PB frequency (PB-low; n=10), RRMS patients with a high peripheral blood PB frequency (PB-high; n=11), and neuromyelitis optica patients (NMO; n=10) as samples, the proportion of follicular helper T ($T_{FH}$) cells among memory CD4-positive T cells (peripheral blood $T_{FH}$ frequency, %) was determined by flow cytometry. $T_{FH}$ cells were defined as CD3+CD4+CD45RA−CCR7+CXCR5+ cells (Morita, R. et al. Human blood CXCR5+CD4+ T cells are counterparts of T follicular cells and contain specific subsets that differentially support antibody secretion. Immunity 2011, 34:108-121). A) shows the method for identifying $T_{FH}$ cells and the peripheral blood $T_{FH}$ frequency in healthy individuals and RRMS patients having a high peripheral blood PB frequency. Each plot shows expression of CCR7 and CXCR5 in memory CD4-positive T cells (CD3+CD4+CD45RA− cells), and the division lines in the plot separate between the CCR7-positive and CCR7-negative groups or the CXCR5-positive and CXCR5-negative groups. The numbers in the plot show the percentages of the respective fractions. The upper right fraction corresponds to $T_{FH}$ cells and the number in this fraction indicates the $T_{FH}$ frequency. B) shows the comparison of peripheral blood $T_{FH}$ frequencies among the groups of interest. The MS patients having a high peripheral blood PB frequency showed significantly higher measured values than healthy individuals, but were divided into a $T_{FH}$-high group (shown by open triangles) showing measured values equal to or higher than a cutoff value (shown by a dashed line) that was defined as the mean+2 standard deviations (SD) of the healthy individuals (28.2%), and a $T_{FH}$-low group (shown by filled triangles) showing measured values lower than this reference. The $T_{FH}$ frequencies observed in most neuromyelitis optica patients are equal to or lower than this cutoff value. Therefore, among the RRMS patients who show an increase in peripheral blood PBs like neuromyelitis optica patients, those in the $T_{FH}$-low group are presumed to have pathological conditions closer to those of neuromyelitis optica patients. The horizontal lines in the graph indicate the mean values. *p<0.05 by one-way ANOVA with post-hoc Turkey's test.

Hereinafter, the present invention will be described in detail.

The present invention relates to markers for determining whether or not the treatment of multiple sclerosis with an IL-6 inhibitor is applicable. Specifically, the present invention relates to use of an immature plasmablast indicator in determining the therapeutic effect of an IL-6 inhibitor on multiple sclerosis. The "immature plasmablast indicator" of the present invention includes at least one or both of the following:

amount of plasmablasts; and
indicator of change in immature plasmablasts.

In the present invention, when the indicator of change in immature plasmablasts is high in patients with multiple sclerosis having a high amount of plasmablasts, the therapeutic effect of an IL-6 inhibitor on multiple sclerosis is determined to be high. In the present invention, "indicator of change in immature plasmablasts" is not particularly limited so long as it can be used to determine the amount of immature plasmablasts or the amount of change in immature plasmablasts in a biological sample. Examples of the "indicator of change in immature plasmablasts" of the present invention include the amplitude of change of immature plasmablasts and the amount of follicular helper T cells (for example, the ratio of follicular helper T cells to CD4+ T cells), but are not limited thereto. In the present invention, when the amount of follicular helper T cells is small, the indicator of change in immature plasmablasts is determined to be high and the therapeutic effect of an IL-6 inhibitor on multiple sclerosis is determined to be high. Furthermore, in the present invention, when the amount of immature plasmablasts is increased due to administration of an IL-6 inhibitor or when the amount of increase in immature plasmablasts is large, the indicator of change in immature plasmablasts is determined to be high and the therapeutic effect of the IL-6 inhibitor on multiple sclerosis is determined to be high.

Alternatively, the present invention relates to methods for predicting or determining the therapeutic effect or applicability of a treatment of multiple sclerosis based on an immature plasmablast indicator in a biological sample derived from a multiple sclerosis patient.

More specifically, the present invention relates to use of an immature plasmablast indicator in determining the therapeutic effect of an IL-6 inhibitor on multiple sclerosis, wherein:

(i) the amount of plasmablasts and/or an indicator of change in immature plasmablasts contained in a biological sample isolated from a multiple sclerosis patient is measured; and (ii) the therapeutic effect of the IL-6 inhibitor is shown to be high for a group of high-plasmablast-level patients having a high amount of plasmablasts as compared with a healthy individual when the indicator of change in immature plasmablasts is determined to be high.

The above-mentioned (i) can be rephrased as "an indicator of change in immature plasmablasts contained in a biological sample isolated from a relapsing-remitting multiple sclerosis patient having a high amount of plasmablasts is measured".

The present invention also relates to a method for predicting the therapeutic effect of an IL-6 inhibitor on a multiple sclerosis patient, which comprises the steps of:

(i) measuring the amount of plasmablasts and/or an indicator of change in immature plasmablasts contained in a biological sample isolated from a multiple sclerosis patient; and (ii) predicting that the therapeutic effect of the IL-6 inhibitor is high for a group of high-plasmablast-level patients having a high amount of plasmablasts as compared with a healthy individual when the indicator of change in immature plasmablasts is determined to be high.

Alternatively, after step (ii), the present invention can further include:

(iii) administering the IL-6 inhibitor to a multiple sclerosis patient shown to be highly effectively treated by the IL-6 inhibitor. More specifically, the present invention relates to a method for treating multiple sclerosis, which comprises steps (i) to (iii).

Alternatively, the present invention relates to use of a detection reagent of an immature plasmablast indicator in the production of an agent for predicting the therapeutic effect of an IL-6 inhibitor on multiple sclerosis.

Alternatively, the present invention relates to use of a detection reagent of an immature plasmablast indicator in predicting or determining the therapeutic effect of an IL-6 inhibitor on multiple sclerosis.

Alternatively, the present invention relates to use of a detection reagent of an immature plasmablast indicator in predicting or determining the therapeutic effect of an IL-6 inhibitor on multiple sclerosis, wherein:

(i) the amount of plasmablasts and/or an indicator of change in immature plasmablasts contained in a biological sample isolated from a relapsing-remitting multiple sclerosis patient is measured;

(ii) the therapeutic effect of the IL-6 inhibitor is shown to be high for a group of high-plasmablast-level patients having a high amount of plasmablasts as compared with a healthy individual when the indicator of change in immature plasmablasts is determined to be high; and (iii) the IL-6 inhibitor is administered to a multiple sclerosis patient shown to be highly effectively treated by the IL-6 inhibitor.

The present invention also relates to use of an IL-6 inhibitor in the treatment of multiple sclerosis, wherein:

(i) the amount of plasmablasts and/or an indicator of change in immature plasmablasts contained in a biological sample isolated from a multiple sclerosis patient is measured;

(ii) the therapeutic effect of the IL-6 inhibitor is shown to be high for a group of high-plasmablast-level patients having a high amount of plasmablasts as compared with a healthy individual when the indicator of change in immature plasmablasts is determined to be high; and (iii) the IL-6 inhibitor is administered to a multiple sclerosis patient shown to be highly effectively treated by the IL-6 inhibitor.

Alternatively, the present invention relates to use of a detection reagent of an immature plasmablast indicator in the production of an agent for predicting the therapeutic effect of an IL-6 inhibitor on multiple sclerosis, wherein:

(i) the amount of plasmablasts and/or an indicator of change in immature plasmablasts contained in a biological sample isolated from a multiple sclerosis patient is measured;

(ii) the therapeutic effect of the IL-6 inhibitor is shown to be high for a group of high-plasmablast-level patients having a high amount of plasmablasts as compared with a healthy individual when the indicator of change in immature plasmablasts is determined to be high; and (iii) the IL-6 inhibitor is administered to a multiple sclerosis patient shown to be highly effectively treated by the IL-6 inhibitor.

The present invention also relates to use of an IL-6 inhibitor in the production of an agent for treating multiple sclerosis, wherein:

(i) the amount of plasmablasts and/or an indicator of change in immature plasmablasts contained in a biological sample isolated from a multiple sclerosis patient is measured;

(ii) the therapeutic effect of the IL-6 inhibitor is shown to be high for a group of high-plasmablast-level patients having a high amount of plasmablasts as compared with a healthy individual when the indicator of change in immature plasmablasts is determined to be high; and (iii) the IL-6 inhibitor is administered to a multiple sclerosis patient shown to be highly effectively treated by the IL-6 inhibitor.

Alternatively, the present invention relates to a method for detecting a marker for predicting the therapeutic effect of an IL-6 inhibitor on multiple sclerosis, the method comprising the step of measuring the amount of plasmablasts and/or an indicator of change in immature plasmablasts contained in a biological sample isolated from a multiple sclerosis patient.

Alternatively, the present invention relates to an IL-6 inhibitor or an agent for treating multiple sclerosis for use in the administration to a multiple sclerosis patient shown to be highly effectively treated by the IL-6 inhibitor by a method comprising the following steps, or for use in the treatment of multiple sclerosis for which the effect of treatment by the IL-6 inhibitor has been shown to be high by a method comprising the following steps:

(i) measuring the amount of plasmablasts and/or an indicator of change in immature plasmablasts contained in a biological sample isolated from a multiple sclerosis patient; and (ii) showing that the therapeutic effect of the IL-6 inhibitor is high for a group of high-plasmablast-level patients having a high amount of plasmablasts as compared with a healthy individual when the indicator of change in immature plasmablasts is determined to be high.

After step (ii), the present invention can further include:

(iii) administering the IL-6 inhibitor or the agent for treating multiple sclerosis to a multiple sclerosis patient shown to be highly effectively treated by the IL-6 inhibitor.

Alternatively, the present invention relates to an agent for treating multiple sclerosis comprising an IL-6 inhibitor as an active ingredient, wherein:

(i) the amount of plasmablasts and/or an indicator of change in immature plasmablasts contained in a biological sample isolated from a multiple sclerosis patient is measured;

(ii) the therapeutic effect of the IL-6 inhibitor is shown to be high for a group of high-plasmablast-level patients having a high amount of plasmablasts as compared with a healthy individual when the indicator of change in immature plasmablasts is determined to be high; and (iii) the agent is administered to a multiple sclerosis patient shown to be highly effectively treated by the IL-6 inhibitor.

Alternatively, the present invention relates to an agent for predicting the therapeutic effect of an IL-6 inhibitor on multiple sclerosis comprising a plasmablast detection reagent and/or a detection reagent for an indicator of change in immature plasmablasts, wherein:

(i) the amount of plasmablasts and/or an indicator of change in immature plasmablasts contained in a biological sample isolated from a multiple sclerosis patient is measured;

(ii) the therapeutic effect of the IL-6 inhibitor is shown to be high for a group of high-plasmablast-level patients having a high amount of plasmablasts as compared with a healthy individual when the indicator of change in immature plasmablasts is determined to be high; and (iii) the IL-6 inhibitor is administered to a multiple sclerosis patient shown to be highly effectively treated by the IL-6 inhibitor.

In the present invention, the method for predicting the therapeutic effect can be rephrased as a method for predicting prognosis, a method for determining whether or not a treatment can be applied, a method for diagnosing the therapeutic effect, a method for determining whether or not a treatment can be continued, etc.

In the present invention, the expression "shown to be highly effectively treated" can be rephrased as "determined to be highly effectively treated".

In the present invention, the "multiple sclerosis patient shown to be highly effectively treated by an IL-6 inhibitor" can be rephrased as a "patient to whom treatment with an IL-6 inhibitor is applicable", an "IL-6 inhibitor-responsive patient", etc. Accordingly, the present invention relates to a method for identifying a patient to whom treatment of multiple sclerosis with an IL-6 inhibitor is applicable, the method comprising the steps of:

(i) measuring the amount of plasmablasts and/or an indicator of change in immature plasmablasts contained in a biological sample isolated from a multiple sclerosis patient; and (ii) showing that the therapeutic effect of the IL-6 inhibitor is high for a group of high-plasmablast-level patients having a high amount of plasmablasts as compared with a healthy individual when the indicator of change in immature plasmablasts is determined to be high.

In the present invention, the amount of plasmablasts (PBs) and/or the indicator of change in immature plasmablasts (immature PBs) contained in a biological sample isolated from a multiple sclerosis patient are measured. The "biological sample" according to the present invention is not particularly limited as long as the biological sample can be collected from a patient and permits measurement of PBs and the indicator of change in immature PBs. Examples of such a sample can include, but are not limited to, blood-derived samples. The blood-derived samples are not limited as long as they contain lymphocytes, and examples are preferably peripheral blood and whole blood, and particularly preferably peripheral blood. Methods for obtaining blood-derived samples from test subjects are well known to those skilled in the art.

In the present invention, examples of multiple sclerosis include but are not limited to relapsing-remitting multiple sclerosis and secondary-progressive multiple sclerosis. In the present invention, relapsing-remitting multiple sclerosis refers to multiple sclerosis with repetitive relapses and remissions. In the present invention, a relapsing-remitting multiple sclerosis patient can also be referred to as a "test subject suspected of having relapsing-remitting multiple sclerosis" or a "patient in need of treatment of relapsing-remitting multiple sclerosis". The "relapsing-remitting multiple sclerosis patient" of the present invention can be, but is not limited to, a patient with relapsing-remitting multiple sclerosis that is not serum aquaporin-4 antibody-positive neuromyelitis optica. Examples of the relapsing-remitting multiple sclerosis of the present invention include, but are not limited to, relapsing-remitting multiple sclerosis in which the amount of plasmablasts contained in a biological sample derived from a patient is high.

Plasmablasts (PBs) are a subset of B cells, a type of lymphocytes, and have the specialized function of producing antibodies. Examples of the "plasmablast (PB)" according to the present invention include, but are not limited to, B cells exhibiting $CD19^+CD27^+CD180^-CD38^{high}$ expression. In the present invention, the "amount of plasmablasts (PBs)" refers to the number or ratio of plasmablasts. Specifically, for example, it can be presented as the ratio of the number of plasmablasts (PBs) to the number of $CD19^+$ B cells in peripheral blood (the number of plasmablasts (PBs)/the number of $CD19^+$ B cells×100(%)). In the present invention, the amount of plasmablasts (PBs) can also be referred to as the ratio of the number of plasmablasts (PBs) to the number of $CD19^+$ B cells, or simply as the plasmablast (PB) ratio, plasmablast (PB) frequency, etc.

In the present invention, the phrases "the amount of plasmablasts (PBs) is high", "a high amount of plasmablasts (PBs)", and "the plasmablast (PB) frequency is high" mean that the amount of PBs contained in a biological sample isolated from a relapsing-remitting multiple sclerosis patient is equal to or higher than the average amount of PBs+1SD (SD: standard deviation), more preferably 2SD (SD: standard deviation), in healthy individuals. In the present invention, in the case where the amount of plasmablasts contained in a biological sample isolated from a relapsing-remitting multiple sclerosis patient is represented as the aforementioned ratio of the number of plasmablasts (PBs) to the number of $CD19^+$ B cells in peripheral blood (the number of plasmablasts (PBs)/the number of $CD19^+$ B cells×100(%)), it is shown that the patient is a high-plasmablast-level patient having a high amount of plasmablasts when this ratio is, for example, 3.00% or more, preferably 3.50% or more, particularly preferably 3.94% or more, even more preferably 4.50% or more.

The method for measuring the amount of PBs according to the present invention is not particularly limited and can be carried out, for example, by measuring the amount of B cells in peripheral blood isolated from the patient by flow cytometry analysis using fluorescently labeled antibodies. Specifically, peripheral blood mononuclear cells (PBMC) can be co-stained with a fluorescent anti-CD3 antibody (e.g., anti-CD3-PerCP-Cy5.5: BioLegend, 300430), a CD14 antibody (e.g., anti-CD14-APC: BioLegend, 301808), a CD19 antibody (e.g., anti-CD19-APC-Cy7, BD Biosciences, 348794), a CD27 antibody (e.g., anti-CD27-PE-Cy7, BD Biosciences, 560609), a CD180 antibody (e.g., anti-CD180-PE, BD Biosciences, 551953), and a CD38 antibody (e.g., anti-CD38-FITC, Beckman Coulter, A0778), and cells exhibiting $CD19^+ CD27^+CD180^-CD3^{high}$ expression can be selected.

More specifically, $CD19^+CD27^+CD180^-CD38^{high}$ cells can be obtained by, for example, excluding $CD3^+$ T cells or $CD14^+$ monocytes from PBMCs, selecting $CD19^+CD27^+$ cells, and further selecting $CD180^-CD38^{high}$ cells. For example, cells having a CD19 expression level of $10^3$ or higher are defined as $CD19^+$ cells; B cells having a CD27 expression level of $2\times10^3$ or higher are defined as $CD27^+$ cells; B cells having a CD180 expression level of $2\times10^3$ or lower are defined as $CD180^-$ cells; and B cells having a CD38 expression level of $3\times10^3$ or higher are defined as $CD38^{high}$ cells. According to these criteria, $CD19^+CD27^+CD180^-CD38^{high}$ cells can be obtained. Also, the cells having a CD19 expression level of $10^3$ or higher can be defined as $CD19^+$ B cells. The amount of PBs can be determined, as mentioned above, according to the number of $CD19^+CD27^+CD180^-CD38^{high}$ B cells/the number of $CD19^+$ B cells×100(%).

Examples of the "indicator of change in immature plasmablasts (PBs)" of the present invention include the amount of immature plasmablasts, the amount of change of immature plasmablasts between before and after administration of an IL-6 inhibitor, and the amount of follicular helper T cells. In the present invention, immature plasmablasts (PBs) refer to plasmablasts that have differentiated from B cells but not yet differentiated into mature plasmablasts. In the present invention, the amount of immature plasmablasts and the amount of change thereof can be measured by using as indicators the changes in the expression levels of Ki-67 and HLA-DR or the presence or absence of Ki-67 and HLA-DR expression.

Expression Levels and Presence or Absence of Expression of Ki-67 and HLA-DR

The expression of cell growth marker Ki-67 and MHC class II molecule HLA-DR decreases as plasmablast differentiation progresses. Therefore, the expression levels or the presence or absence of expression of Ki-67 and HLA-DR can be used as indicators to detect and isolate immature plasmablasts. In the present invention, when the proportion of $Ki-67^+HLA-DR^{high}$ cells in peripheral blood PBs contained in a biological sample isolated from a multiple sclerosis patient increases, the indicator of change in immature plasmablasts is shown to be high. In the present invention, the amount of immature plasmablasts can be measured both before and after administration of an IL-6 inhibitor. When administration of an IL-6 inhibitor causes an increase in the amount of immature plasmablasts compared to before the administration, the indicator of change in immature plasmablasts can be determined to be high.

Immature plasmablasts which express Ki-67 and HLA-DR can be detected or obtained, for example, by a method known to those skilled in the art such as flow cytometry. Specifically, for example, but without limitation, immature plasmablasts in the present invention can be detected or obtained by removing Ki-67$^-$ cells and HLA-DR$^-$ cells from PBMCs and selecting Ki-67$^+$HLA-DR$^{high}$ cells.

Amount of Follicular Helper T Cells

The present inventors discovered that treatment with an IL-6 inhibitor is effective in a group of MS patients having a small amount of follicular helper T cells in their peripheral blood when compared with the other groups of patients; and that in the group of RRMS patients having a small amount of follicular helper T cells, the amount of increase in immature PBs is large, or the amount of immature PBs increases. Therefore, the therapeutic effect of an IL-6 inhibitor on MS can be predicted using the amount of follicular helper T cells as an indicator. Furthermore, since the group of patients having a small amount of follicular helper T cells, for whom the therapeutic effect of an IL-6 inhibitor is satisfactory, shows a large amount of increase in the amount of immature PBs or shows an increase in the amount of immature PBs, the amount of follicular helper T cells may become an indicator of change in the amount of immature PBs.

Follicular helper T cells are a subset of CD4+ T cells present at follicular germinal centers in secondary lymphoid tissues, and express CXCR5 and CCR7. The amount of follicular helper T cells in the present invention can be presented, for example, as the proportion of CD3+CD4+ CD45RA−CCR7+CXCR5+ cells to memory CD4+ T cells in peripheral blood. More specifically, the present invention can include the steps of:

(i) measuring CXCR5+CCR7+ cells in memory CD4+ T cells; and (ii) showing that the indicator of change in immature plasmablasts is high when the proportion of CXCR5+ CCR7+ cells in memory CD4+ T cells is low.

In the present invention, when the proportion of CD3+ CD4+CD45RA−CCR7+CXCR5+ cells in memory CD4+ T cells is low, the amount of follicular helper T cells can be determined to be small, and the indicator of change in immature plasmablasts can be determined to be high. Specifically, when the proportion of CD3+CD4+CD45RA− CCR7+CXCR5+ cells in memory CD4+ T cells contained in a biological sample isolated from a relapsing-remitting multiple sclerosis patient is, for example, lower than 30.0%, preferably 28.2%, particularly preferably 26.0%, or more preferably 25.0%, the indicator of change in immature plasmablasts is shown to be high. This proportion can also be determined by using a method known to those skilled in the art, such as flow cytometry which uses peripheral blood and such isolated from the patients as the sample.

In the present invention, plasmablasts can be detected using a plasmablast detection reagent. Furthermore, the indicator of change in immature plasmablasts can be detected using a reagent for detecting the indicator of change in immature plasmablasts. The plasmablast detection reagent and the immature plasmablast detection reagent are not particularly limited as long as the plasmablast and the indicator of change in immature plasmablasts can be detected, and examples include antibodies capable of recognizing the plasmablast and the indicator of change in immature plasmablasts. The antibodies capable of recognizing the plasmablast and the indicator of change in immature plasmablasts are not particularly limited as long as the antibodies can recognize a protein or a receptor expressed on the surface of the plasmablast and the indicator of change in immature plasmablasts. Examples of antibodies that detect plasmablasts include an anti-CD19 antibody, a CD27 antibody, and an anti-CD38 antibody. Furthermore, when the amount of immature plasmablasts or the amount of change of immature plasmablasts is used as the indicator of change in immature plasmablasts, an anti-Ki-67 antibody, an anti-HLA-DR antibody, and such may be used. Alternatively, when follicular helper T cells are used as the indicator of change in immature plasmablasts, antibodies against CXCR5 and CCR7 which are expressed in follicular helper T cells, can be used. When the amount of follicular helper T cells is used as the indicator of change in immature plasmablasts, in case the amount of follicular helper T cells is small or the presence of follicular helper T cells cannot be confirmed, the indicator of change in immature plasmablasts can be determined to be high.

In the present invention, two or more of these antibodies, or three or more of these antibodies are preferably used in combination.

The antibodies in the present invention can be polyclonal antibodies or monoclonal antibodies. Alternatively, the antibodies of the present invention may be multispecific antibodies mutually recognizing different antigenic determinants of proteins or receptors expressed on the surface of plasmablasts.

The present invention also provides a kit for detecting a marker for predicting a therapeutic effect on multiple sclerosis, the kit comprising: (i) a reagent for detecting a plasmablast and/or an indicator of change in immature plasmablasts in a biological sample; and (ii) a positive control sample for the plasmablast and/or the indicator of change in immature plasmablasts.

The kit of the present invention is a kit for detecting a marker for predicting a therapeutic effect on multiple sclerosis, wherein:

(i) the amount of plasmablasts and/or an indicator of change in immature plasmablasts contained in a biological sample isolated from a multiple sclerosis patient is measured;

(ii) the therapeutic effect of an IL-6 inhibitor is shown to be high for a group of high-plasmablast-level patients having a high amount of plasmablasts as compared with a healthy individual when the indicator of change in immature plasmablasts is determined to be high; and (iii) an IL-6 inhibitor is administered to a multiple sclerosis patient shown to be highly effectively treated by the IL-6 inhibitor.

The present invention predicts the therapeutic effect of an IL-6 inhibitor on multiple sclerosis (particularly on relapsing-remitting multiple sclerosis showing a large amount of peripheral blood PBs) by using an immature PB as an indicator. In the present invention, the "IL-6 inhibitor" is not limited as long as the IL-6 inhibitor is capable of blocking IL-6 signal transduction and inhibiting the biological activity of IL-6. Specific examples of the IL-6 inhibitor can include, but are not limited to, a substance that binds to IL-6, a substance that binds to an IL-6 receptor, and a substance that binds to gp130. Other examples of the IL-6 inhibitor can include, but are not limited to, a substance that inhibits phosphorylation of STAT3, which is important for the intracellular signaling of IL-6, for example, AG490. The IL-6 inhibitor includes, without being particularly limited, an anti-IL-6 antibody, an anti-IL-6 receptor antibody, an anti-gp130 antibody, an IL-6 variant, a soluble IL-6 receptor variant, a partial IL-6 peptide, a partial IL-6 receptor peptide, and a low-molecular weight compound exhibiting activity similar thereto.

Examples of the preferred embodiment of the IL-6 inhibitor can include an IL-6 receptor inhibitor, particularly an anti-IL-6 receptor antibody.

The origin of the antibody used in the present invention is not particularly limited, and the antibody can be derived from preferably a mammal, more preferably a human.

The antibody used in the present invention can be obtained as a polyclonal or monoclonal antibody by use of an approach known in the art. The antibody used in the present invention is particularly preferably a mammal-derived monoclonal antibody. The mammal-derived monoclonal antibody includes an antibody produced by a hybridoma, and an antibody produced by a host transformed with an expression vector containing an antibody gene by a genetic engineering approach. Usually, this antibody blocks the transmission of the biological activity of IL-6 into a cell through its binding to IL-6, an IL-6 receptor, gp130, or the like.

Basically, the monoclonal antibody-producing hybridoma can be prepared by use of a technique known in the art as follows: an IL-6 receptor, IL-6, gp130, or the like is used as a sensitizing antigen in immunization according to an ordinary immunization method, and the resulting immunocytes are fused with parent cells known in the art by an ordinary cell fusion method, and the fused cells are screened for monoclonal antibody-producing cells by an ordinary screening method to prepare monoclonal antibody-producing hybridomas.

Specifically, the monoclonal antibody can be prepared as follows: in the case of preparing, for example, an anti-IL-6 receptor antibody, a human IL-6 receptor or mouse IL-6 receptor to be used as a sensitizing antigen is obtained by using the nucleotide sequence of the IL-6 receptor gene and/or the amino acid sequence of the IL-6 receptor protein disclosed in European Patent Application Publication No. EP 325474 or disclosed in JP-A (Kokai) H3-155795, respectively.

There are two types of IL-6 receptor proteins: a protein expressed on the cell membrane, and a protein dissociated from the cell membrane (soluble IL-6 receptor) (Yasukawa, K. et al., J. Biochem. (1990) 108, 673-676). The soluble IL-6 receptor is constituted by substantially the extracellular region of the IL-6 receptor bound with the cell membrane, and differs from the membrane-bound IL-6 receptor in that the soluble IL-6 receptor lacks the transmembrane region or lacks the transmembrane region and the intracellular region. Any IL-6 receptor may be used as the IL-6 receptor protein as long as the IL-6 receptor may be used as a sensitizing antigen in the preparation of an anti-IL-6 receptor antibody used in the present invention.

The gene sequence of the IL-6 receptor is inserted to an expression vector system known in the art, and appropriate host cells are transformed therewith. Then, the IL-6 receptor protein of interest is purified by a method known in the art from the inside of the host cells or from a culture supernatant thereof. This purified IL-6 receptor protein can be used as the sensitizing antigen. Alternatively, cells expressing the IL-6 receptor or a fusion protein of the IL-6 receptor protein with another protein may be used as the sensitizing antigen.

Likewise, in the case of using IL-6 as a sensitizing antigen in antibody obtainment, human IL-6 is obtained by using the nucleotide sequence of the IL-6 gene and/or the amino acid sequence of the IL-6 protein disclosed in Eur. J. Biochem (1987) 168, 543-550, J. Immunol. (1988)140, 1534-1541, or Agr. Biol. Chem. (1990) 54, 2685-2688. Also, the nucleotide sequence of the gp130 gene and/or the amino acid sequence of the gp130 protein disclosed in EP 411946 can be used as a sensitizing antigen for obtaining an anti-gp130 antibody.

The mammal to be immunized with the sensitizing antigen is not particularly limited and is preferably selected in consideration with compatibility with the parent cells for use in cell fusion. In general, a rodent, for example, a mouse, a rat, or a hamster is used.

The animal is immunized with the sensitizing antigen according to a method known in the art. For example, a general method involves intraperitoneally or subcutaneously injecting the sensitizing antigen to the mammal. Specifically, the sensitizing antigen diluted or suspended in an appropriate volume of phosphate-buffered saline (PBS), saline, or the like is mixed, if desired, with an appropriate amount of a usual adjuvant, for example, a complete Freund's adjuvant. After emulsification, several shots of the emulsion are each preferably administered to the mammal every 4 to 21 days. Also, an appropriate carrier can be used in the immunization with the sensitizing antigen.

After such immunization and confirmation of a rise in desired antibody level in serum, immunocytes are collected from the mammal and subjected to cell fusion. Preferred examples of the immunocytes that are subjected to cell fusion particularly include spleen cells.

Mammalian myeloma cells for use as partner parent cells to be fused with the immunocytes have already been known in the art, and various cell lines, for example, P3X63Ag8.653 (Kearney, J. F. et al., J. Immunol. (1979) 123, 1548-1550), P3X63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S. J. Exp. Med. (1978) 148, 313-323), and R210 (Galfre, G. et al., Nature (1979) 277, 131-133) are appropriately used.

Basically, the cell fusion between the immunocytes and the myeloma cells can be carried out according to a method known in the art, for example, the method of Milstein et al. (Kohler. G. and Milstein, C., Methods Enzymol. (1981) 73, 3-46).

More specifically, the cell fusion is carried out, for example, in a usual nutrient medium in the presence of a cell fusion promoter. For example, polyethylene glycol (PEG) or hemagglutinating virus of Japan (HVJ) is used as the fusion promoter. An auxiliary such as dimethyl sulfoxide can be further added thereto and used, if desired, for enhancing fusion efficiency.

The ratio between the immunocytes and the myeloma cells used is preferably set to, for example, 1:1 to 10:1 (immunocytes:myeloma cells). For example, an RPMI1640 medium or a MEM medium suitable for the growth of the myeloma cell lines mentioned above or a usual medium for use in this kind of cell culture can be used in the cell fusion and may be used in combination with a serum supplement such as fetal calf serum (FCS).

For the cell fusion, predetermined amounts of the immunocytes and the myeloma cells are well mixed in the medium. A PEG solution, for example, a solution of PEG having an average molecular weight of about 1000 to 6000, preheated to approximately 37° C. is usually added to the mixture at a concentration of 30 to 60% (w/v) and mixed therewith to form the fusion cells (hybridomas) of interest. Subsequently, the cell fusion agent and the like unfavorable for the growth of the hybridomas can be removed by repeating the operation of sequentially adding an appropriate medium and removing a supernatant by centrifugation.

The hybridomas thus obtained are cultured in a usual selective medium, for example, a HAT medium (medium containing hypoxanthine, aminopterin, and thymidine) for selection. This culture in the HAT medium is continued for a period (usually, several days to several weeks) sufficient for killing cells (non-fused cells) other than the hybridomas of interest. Subsequently, hybridomas producing the antibody of interest are screened for and cloned by an ordinary limiting dilution method.

In addition to obtaining such hybridomas by immunizing a non-human animal with an antigen, a desired human antibody having binding activity against a desired antigen or against cells expressing the antigen may be obtained by sensitizing in vitro human lymphocytes with the desired antigen protein or cells expressing the antigen and fusing the sensitized B lymphocytes with human myeloma cells, for example, with U266 (see JP-A (Kokai) H1-59878). Alternatively, the antigen or cells expressing the antigen may be administered to a transgenic animal having a human antibody gene repertoire, and the desired human antibody can be obtained according to the method mentioned above (see International Patent Application Publication Nos. WO93/12227, WO92/03918, WO94/02602, WO94/25585, WO96/34096, and WO96/33735).

The monoclonal antibody-producing hybridomas thus prepared can be passaged in a usual medium and can also be preserved for a long period in liquid nitrogen.

The monoclonal antibody is obtained from the hybridomas by employing, for example, a method which involves culturing the hybridomas according to an ordinary method and obtaining the antibody as a culture supernatant thereof, or a method which involves administering the hybridomas to mammals compatible therewith and, after growth, obtaining the antibody as ascitic fluid thereof. The former method is suitable for obtaining a highly pure antibody, while the latter method is suitable for the large-scale production of the antibody.

For example, hybridomas producing an anti-IL-6 receptor antibody can be prepared by a method disclosed in JP-A (Kokai) H3-139293. This preparation can be carried out by a method which involves intraperitoneally injecting PM-1 antibody-producing hybridomas to BALB/c mice to obtain ascitic fluid, and purifying the PM-1 antibody from the ascitic fluid, or a method which involves culturing the hybridomas in an appropriate medium, for example, an RPMI1640 medium containing 10% fetal calf serum and 5% BM-Condimed H1 (manufactured by Boehringer Mannheim), a Hybridoma SFM medium (manufactured by Gibco BRL/Life Technologies, Inc.), or a PFHM-II medium (manufactured by Gibco BRL/Life Technologies, Inc.) and purifying the PM-1 antibody from the culture supernatant.

In the present invention, a recombinant antibody produced by use of a gene recombination technique which involves cloning an antibody gene from hybridomas, incorporating the antibody gene into an appropriate vector, and transferring this vector to a host can be used as the monoclonal antibody (see e.g., Borrebaeck C. A. K. and Larrick J. W. THERAPEUTIC MONOCLONAL ANTIBODIES, Published in the United Kingdom by MACMILLAN PUBLISHERS LTD, 1990).

Specifically, mRNAs encoding the variable (V) regions of the antibody are isolated from cells, for example, hybridomas, producing the antibody of interest. For the mRNA isolation, total RNA is prepared by a method known in the art, for example, a guanidine ultracentrifugation method (Chirgwin, J. M. et al., Biochemistry (1979) 18, 5294-5299) or an AGPC method (Chomczynski, P. et al., Anal. Biochem. (1987) 162, 156-159), and the mRNAs are prepared using mRNA Purification Kit (manufactured by Pharmacia Corp.) or the like. Alternatively, the mRNAs can be directly prepared by use of QuickPrep mRNA Purification Kit (manufactured by Pharmacia Corp.).

Antibody V region cDNAs are synthesized from the obtained mRNAs using reverse transcriptase. The cDNA synthesis can be carried out using AMV Reverse Transcriptase First-strand cDNA Synthesis Kit or the like. Also, 5'-Ampli FINDER RACE Kit (manufactured by Clontech Laboratories, Inc.) and a PCR-based 5'-RACE method (Frohman, M. A. et al., Proc. Natl. Acad. Sci. USA (1988) 85, 8998-9002; and Belyaysky, A. et al., Nucleic Acids Res. (1989) 17, 2919-2932) can be used in the cDNA synthesis and amplification. The DNA fragments of interest are purified from the obtained PCR products and ligated with vector DNAs. Recombinant vectors are thereby prepared and transferred to *E. coli* or the like. Colonies are selected, and desired recombinant vectors are prepared. The nucleotide sequences of the DNAs of interest are confirmed by a method known in the art, for example, a deoxy method.

If DNAs encoding the V regions of the antibody of interest are obtained, these DNAs are linked to DNAs encoding constant regions (C regions) of a desired antibody, and these linked DNAs are incorporated into expression vectors. Alternatively, the DNAs encoding the antibody V regions may be incorporated into expression vectors containing the DNAs of the antibody C regions.

For the production of the antibody used in the present invention, the antibody gene is incorporated into an expression vector such that the antibody gene is expressed under the control of expression control regions, for example, an enhancer and a promoter, as mentioned later. Next, host cells are transformed with this expression vector, and the antibody can be expressed.

In the present invention, a recombinant antibody that has been artificially engineered for the purpose of, for example, reducing the heterologous antigenicity against humans, for example, a chimeric antibody or a humanized antibody, can be used. Such an engineered antibody can be produced by use of a known method.

A chimeric antibody is obtained by linking the antibody V region-encoding DNAs obtained as described above to human antibody C region-encoding DNAs, and incorporating the linked DNAs into expression vectors, which are then introduced into a host, followed by production of the antibody (see EP125023 and WO92-19759). A chimeric antibody useful in the present invention can be obtained by use of this known method.

The humanized antibody, is also called reshaped human antibody or antibody made into human type antibody, and is obtained by grafting the complementarity-determining regions (CDRs) of a non-human mammalian antibody, for example, a mouse antibody, to the complementarity-determining regions of a human antibody. A general gene recombination approach therefor is also known (see EP125023 and WO92-19759).

Specifically, DNA sequences designed so as to link mouse antibody CDRs and human antibody framework regions (FRs) are synthesized by PCR using several prepared oligonucleotides having overlapping terminal portions. The obtained DNAs are linked to DNAs encoding human antibody C regions. Subsequently, the linked DNAs are incorporated into expression vectors, which are then transferred to a host, followed by the production of the antibody to obtain the humanized antibody (see EP239400 and WO92-19759).

The human antibody FRs to be connected via CDRs are selected such that the complementarity-determining regions form a favorable antigen-binding site. If necessary, amino acids in the framework regions of the antibody variable regions may be substituted such that the complementarity-determining regions of the resulting reshaped human antibody form an appropriate antigen-binding site (Sato, K. et al., Cancer Res. (1993) 53, 851-856).

Usually, human antibody C regions are used for the chimeric antibody or the humanized antibody. Examples of the human antibody heavy chain C region include Cγ. For example, Cγ1, Cγ2, Cγ3, or Cγ4 can be used. Examples of the human antibody light chain C region can include κ and λ. These human antibody C regions may be modified in order to improve the stability of the antibody or the stability of production thereof.

A chimeric antibody is composed of the variable regions of a non-human mammal-derived antibody and human antibody-derived C regions. A humanized antibody is composed of the complementarity-determining regions of a non-human mammal-derived antibody and human antibody-derived framework regions and C regions. These antibodies exhibit reduced antigenicity in human bodies and as such, are useful as antibodies for use as pharmaceuticals.

Preferable specific examples of the humanized antibody used in the present invention include humanized PM-1 antibodies (see WO92-19759).

In addition to the aforementioned methods for obtaining a human antibody, a technique of obtaining a human antibody by panning using a human antibody library is also known. For example, human antibody variable regions are expressed as a single-chain antibody (scFv) on the surface of phages by a phage display method, and a phage binding to the antigen may be selected. The gene of the selected phage can be analyzed to determine DNA sequences encoding the variable regions of the human antibody binding to the antigen. If the DNA sequence of scFv binding to the antigen is revealed, an appropriate expression vector containing this sequence can be prepared to obtain the human antibody. These methods have already been well known. See WO92/01047, WO92/20791, WO93/06213, WO93/11236, WO93/19172, WO95/01438, and WO95/15388.

The antibody gene constructed as described above can be expressed by a method known in the art. In the case of using mammalian cells, the antibody gene can be expressed by use of a DNA in which a routinely used useful promoter, the antibody gene to be expressed, and a poly-A signal 3'-downstream thereof are functionally linked, or by use of a vector containing the DNA. Examples of the promoter/enhancer can include human cytomegalovirus immediate early promoter/enhancer.

Alternatively, a promoter/enhancer of a virus such as retrovirus, polyoma virus, adenovirus, or simian virus 40 (SV40), a mammalian cell-derived promoter/enhancer such as human elongation factor 1α (HEF1α), or the like can be used as the promoter/enhancer for the antibody expression used in the present invention.

In the case of using, for example, the SV40 promoter/enhancer, the antibody expression can be readily carried out according to the method of Mulligan et al. (Mulligan, R. C. et al., Nature (1979) 277, 108-114). In the case of using the HEF1α promoter/enhancer, the antibody expression can be readily carried out according to the method of Mizushima et al. (Mizushima, S. and Nagata, S. Nucleic Acids Res. (1990) 18, 5322).

In the case of using prokaryotic cells as the host, bacterial cells can be used in the production system. *E. coli* and *Bacillus subtilis* are known as the bacterial cells.

For *E. Coli*, a routinely used useful promoter, a signal sequence for antibody secretion, and the antibody gene to be expressed can be functionally linked and expressed. Examples of the promoter can include lacZ promoter and araB promoter. In the case of using the lacZ promoter, the method of Ward et al. (Ward, E. S. et al., Nature (1989) 341, 544-546; and Ward, E. S. et al. FASEB J. (1992) 6, 2422-2427) can be followed. In the case of using the araB promoter, the method of Better et al. (Better, M. et al. Science (1988) 240, 1041-1043) can be followed.

In the case of production in the periplasm of *E. coli*, pelB signal sequence (Lei, S. P. et al., J. Bacteriol. (1987) 169, 4379-4383) can be used as the signal sequence for antibody secretion. The antibodies produced in the periplasm are separated and then used after appropriate refolding of the antibody structure (see e.g., WO96/30394).

A replication origin derived from SV40, polyoma virus, adenovirus, bovine papillomavirus (BPV), or the like can be used. The expression vector can contain a selective marker such as aminoglycoside phosphotransferase (APH) gene, thymidine kinase (TK) gene, *E. coli* xanthine guanine phosphoribosyltransferase (Ecogpt) gene, or dihydrofolate reductase (dhfr) gene in order to amplify the number of gene copies in the host cell system.

For the production of the antibody used in the present invention, an arbitrary production system can be used. There are in vitro and in vivo production systems for antibody production. Examples of the in vitro production system include a production system using eukaryotic cells and a production system using prokaryotic cells.

In the case of using eukaryotic cells as the host, animal cells, plant cells, or fungal cells can be used in the production system. (1) Mammalian cells, for example, CHO, COS, myeloma, baby hamster kidney (BHK), HeLa, and Vero, (2) amphibian cells, for example, *Xenopus* oocytes, or (3) insect cells, for example, sf9, sf21, and Tn5 are known as the animal cells. *Nicotiana tabacum*-derived cells are known as the plant cells and can be callus-cultured. Yeasts of, for example, the genus *Saccharomyces* (e.g., *Saccharomyces cerevisiae*) or filamentous fungi of, for example, the genus *Aspergillus* (e.g., *Aspergillus niger*) are known as the fungal cells.

The antibody gene of interest is transferred to these cells by transformation, and the transformed cells are cultured in vitro to obtain the antibody. This culture is carried out according to a method known in the art. For example, DMEM, MEM, RPMI1640, or IMDM can be used as a medium and may be used in combination with a serum supplement such as fetal calf serum (FCS). Alternatively, the cells thus harboring the antibody gene may be transferred to the peritoneal cavity or the like of an animal so that the antibody is produced in vivo.

On the other hand, examples of the in vivo production system include a production system using an animal and a production system using a plant. When an animal is used, a mammal, an insect, or the like can be used in the production system.

A goat, a pig, sheep, a mouse, cattle, or the like can be used as the mammal (Vicki Glaser, SPECTRUM Biotechnology Applications, 1993). A silkworm can be used as the insect. In the case of using the plant, for example, tobacco can be used.

The antibody gene is introduced into such an animal or a plant, and the antibody is produced in the body of the animal or the plant and recovered. For example, the antibody gene is prepared as a fusion gene by inserting the gene midway into a gene encoding a protein specifically produced in milk, such as goat β casein. A DNA fragment that contains the fusion gene having the inserted antibody gene is injected into a goat embryo, and this embryo is introduced into a female goat. The desired antibody is obtained from milk produced by a transgenic goat born from the embryo-recipient goat, or progeny thereof. Hormones may be appropriately used for the transgenic goat in order to increase the amount of the milk containing the desired antibody produced by the transgenic goat (Ebert, K. M. et al., Bio/Technology (1994) 12, 699-702).

In the case of using a silkworm, a silkworm is infected with baculovirus having an insert of the antibody gene of interest, and the desired antibody is obtained from the body fluid of this silkworm (Maeda, S. et al., Nature (1985) 315, 592-594). In the case of using tobacco, the antibody gene of interest is inserted to a vector for expression in plants, for example, pMON530, and this vector is introduced into a bacterium such as *Agrobacterium tumefaciens*. Tobacco, for example, *Nicotiana tabacum*, is infected with this bacterium, and the desired antibody is obtained from the leaf of this tobacco (Julian, K.-C. Ma et al., Eur. J. Immunol. (1994)24, 131-138).

In the case of producing an antibody in the in vitro or in vivo production system as mentioned above, an antibody heavy chain (H chain)-encoding DNA and an antibody light chain (L chain)-encoding DNA may be incorporated into separate expression vectors, and the host can be co-transformed with these expression vectors. Alternatively, the H chain-encoding DNA and the L chain-encoding DNA may be incorporated into a single expression vector, and the host can be transformed with this expression vector (see WO94-11523).

The antibody used in the present invention may be a fragment of the antibody or a modified form of the antibody as long as the fragment or the modified form can be suitably used in the present invention. Examples of the antibody fragment include Fab, F(ab')2, Fv, and single-chain Fv (scFv) containing H and L chain Fvs linked through an appropriate linker.

Specifically, the antibody fragment is formed by the treatment of the antibody with an enzyme, for example, papain or pepsin, or is expressed in appropriate host cells after construction of a gene encoding the antibody fragment and subsequent transfer of this gene to an expression vector (see e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 497-515; Lamoyi, E., Methods in Enzymology (1989) 121, 652-663; Rousseaux, J. et al., Methods in Enzymology (1989) 121, 663-66; and Bird, R. E. et al., TIBTECH (1991) 9, 132-137).

An scFv is obtained by linking the H chain V region and the L chain V region of an antibody. In this scFv, the H chain V region and the L chain V region are linked via a linker, preferably a peptide linker (Huston, J. S. et al., Proc. Natl. Acad. Sci. U.S.A. (1988) 85, 5879-5883). The H chain V region and the L chain V region in the scFv may be derived from any of the above-described antibodies according to the present invention. For example, an arbitrary single-chain peptide composed of 12 to 19 amino acid residues is used as the peptide linker for linking the V regions.

A DNA encoding the scFv is obtained by using a DNA encoding the H chain or the H chain V region of the aforementioned antibody and a DNA encoding the L chain or the L chain V region of the antibody as templates, and amplifying from each of those sequences a DNA portion encoding the desired amino acid sequence by PCR using a primer pair defining the two ends thereof, followed by further amplification using a DNA encoding the peptide linker portion and a primer pair that is designed such that each of the two ends of the peptide linker is linked to the H chain and the L chain, respectively.

Once the scFv-encoding DNA is prepared, an expression vector containing the DNA, and a host transformed with the expression vector can be obtained according to routine methods. Also, the scFv can be obtained according to a routine method using the host.

These antibody fragments can be produced through obtainment and expression of their genes and production by the host in the same way as above. The "antibody" according to the present invention also encompasses these antibody fragments.

Antibodies bound with various molecules such as polyethylene glycol (PEG) may be used as modified forms of antibody. The "antibody" according to the present invention also encompasses these modified forms of the antibody. Such a modified form of the antibody can be obtained by chemical modification of the obtained antibody. These methods have already been established in the art.

The antibody produced and expressed as described above can be separated from the inside or outside of the cells or from the host and purified to homogeneity. The separation and purification of the antibody used in the present invention can be carried out by affinity chromatography. Examples of columns for use in the affinity chromatography include protein A columns and protein G columns. Examples of carriers for use in the protein A columns include Hyper D, POROS, and Sepharose F.F. Any of other ordinary separation and purification methods for use in proteins can be used without limitation.

For example, the antibody used in the present invention can be separated and purified by appropriately selecting or combining chromatography other than the affinity chromatography, filters, ultrafiltration, salting out, and/or dialysis. Examples of the chromatography include ion-exchange chromatography, hydrophobic chromatography, and gel filtration. These chromatography techniques are applicable to high-performance liquid chromatography (HPLC). Alternatively, reverse-phase HPLC may be used.

The concentration of the antibody thus obtained can be measured by, for example, absorbance measurement or ELISA. Specifically, in the case of measuring the concentration by the absorbance measurement, the absorbance is measured at 280 nm after appropriate dilution of the antibody with PBS(−), and the concentration is calculated assuming that 1 mg/ml is 1.35 OD. Alternatively, the concentration can be measured by ELISA as follows: 100 µl of goat anti-human IgG (manufactured by TAG) diluted to 1 µg/ml with a 0.1 M bicarbonate buffer solution (pH 9.6) is added to a 96-well plate (manufactured by Nunc/Thermo Fisher Scientific, Inc.) and incubated overnight at 4° C. to immobilize the antibody thereon. After blocking, 100 µl of an appropriately diluted antibody used in the present invention or a sample containing the antibody, or a preparation human IgG (manufactured by Cappel Laboratories, Inc.) is added thereto and incubated at room temperature for 1 hour.

After washing, 100 μl of alkaline phosphatase-labeled anti-human IgG (manufactured by BioSource International, Inc.) diluted 5000-fold is added thereto and incubated at room temperature for 1 hour. After washing, a substrate solution is added thereto and incubated. Then, the absorbance is measured at 405 nm using MICROPLATE READER Model 3550 (manufactured by Bio-Rad Laboratories, Inc.) to calculate the concentration of the antibody of interest.

Specific examples of the anti-IL-6 antibody can include, but are not particularly limited to, MH166 (Matsuda, T. et al., Eur. J. Immunol. (1998) 18, 951-956) and SK2 antibody (Sato K et al., Academic proceedings of the 21st General Meeting of the Japanese Society for Immunology (1991) 21, 166).

Specific examples of the anti-IL-6 receptor antibody include, but are not particularly limited to, MR16-1 antibody (Tamura, T. et al. Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 antibody, and AUK146-15 antibody (WO92-19759). Among them, preferred examples of the monoclonal antibody against the human IL-6 receptor include, but are not limited to, the PM-1 antibody, and preferred examples of the monoclonal antibody against the mouse IL-6 receptor include, but are not limited to, the MR16-1 antibody. Preferred examples of the humanized anti-IL-6 receptor antibody can include, but are not limited to, a humanized PM-1 antibody (Tocilizumab, MRA). Other preferred examples of the humanized anti-IL-6 receptor antibody can include, but are not limited to, antibodies described in WO2009/041621 and WO2010/035769. Examples of other preferred embodiments of the anti-IL-6 receptor antibody can include, but are not limited to, an anti-IL-6 receptor antibody that recognizes the same epitope as that recognized by the humanized PM-1 antibody (Tocilizumab, MRA).

Specific examples of the anti-gp130 antibody include, but are not particularly limited to, AM64 antibody (JP-A (Kokai) H3-219894), 4B11 antibody, 2H4 antibody (U.S. Pat. No. 5,571,513), and B-P8 antibody (JP-A (Kokai) H8-291199).

The IL-6 variant used in the present invention is a substance that has binding activity with the IL-6 receptor and does not transduce the biological activity of IL-6. Thus, the IL-6 variant blocks the signal transduction of IL-6 because it competes with IL-6 for binding to the IL-6 receptor but does not transduce the biological activity of IL-6.

An IL-6 variant is prepared by introducing mutations into IL-6 through substitution of amino acid residues in the amino acid sequence of IL-6. The origin of IL-6 on which the IL-6 variant is based is not limited and is preferably human IL-6 in consideration of antigenicity, etc. Specifically, the secondary structure of the amino acid sequence of IL-6 is predicted by use of a molecular modeling program known in the art, for example, WHATIF (Vriend et al., J. Mol. Graphics (1990) 8, 52-56), and the influence of amino acid residues to be substituted on the whole structure is evaluated. After determination of appropriate amino acid residues to be substituted, a vector containing a nucleotide sequence encoding the human IL-6 gene is used as a template, and a conventional PCR method is performed to introduce mutations such that the amino acids are substituted, and thereby a gene encoding the IL-6 variant is obtained. This gene is incorporated into an appropriate expression vector according to the need, and the IL-6 variant can be obtained according to the aforementioned expression, production, and purification methods for the recombinant antibody.

Specific examples of the IL-6 variant can include IL-6 variants disclosed in Brakenhoff et al., J. Biol. Chem. (1994) 269, 86-93, Savino et al., EMBO J. (1994) 13, 1357-1367, WO96-18648, and WO96-17869.

A partial IL-6 receptor peptide is a peptide having a portion or the whole of the amino acid sequence of a region involved in the binding of the IL-6 receptor to IL-6 in the amino acid sequence of the IL-6 receptor. Such a peptide is composed of usually 10 to 80, preferably 20 to 50, more preferably 20 to 40 amino acid residues.

The partial IL-6 receptor peptide can be prepared by identifying the region involved in the binding of the IL-6 receptor to IL-6 in the amino acid sequence of the IL-6 receptor and producing the peptide by a conventionally known method, for example, a genetic engineering approach or a peptide synthesis method on the basis of a portion or the whole of the amino acid sequence of the identified region.

For the preparation of the partial IL-6 receptor peptide by the genetic engineering approach, a DNA sequence encoding the desired peptide is incorporated into an expression vector, and the partial IL-6 receptor peptide can be obtained according to the aforementioned expression, production, and purification methods for the recombinant antibody.

For the preparation of the partial IL-6 receptor peptide by the peptide synthesis method, a method conventionally used in peptide synthesis, for example, a solid-phase synthesis method or a liquid-phase synthesis method can be used.

Specifically, the peptide synthesis can be carried out according to methods described in Zoku Iyakuhin no Kaihatsu (Development of Pharmaceuticals, Second Series, in English), Vol. 14, Peptide Synthesis, edited by Haruaki Yajima, Hirokawa Shoten Co., Ltd. (1991). The solid-phase synthesis method used is a method which involves, for example, coupling an amino acid corresponding to the C terminus of a peptide to be synthesized to a support insoluble in an organic solvent, and elongating a peptide chain by alternately repeating the reaction of condensing one amino acid at a time (its α-amino group and side chain functional groups have been protected with appropriate protective groups) in a direction from the C terminus toward the N terminus and the reaction of eliminating the protective group of the α-amino group of the amino acid or peptide bound onto the resin. The solid-phase peptide synthesis method is broadly divided into Boc and Fmoc methods depending on the types of the protective groups used.

After such synthesis of the peptide of interest, deprotection reaction and cleavage reaction of the peptide chain from the support are carried out. In the cleavage reaction of the peptide chain, usually, hydrogen fluoride or trifluoromethanesulfonic acid can be used for the Boc method, and TFA can be used for the Fmoc method. In the Boc method, the protected peptide resin is treated, for example, in the presence of anisole in hydrogen fluoride. Subsequently, protective group elimination and cleavage from the support are carried out to recover the peptide. This peptide is freeze-dried to obtain a crude peptide. On the other hand, in the Fmoc method, for example, deprotection reaction and cleavage reaction of the peptide chain from the support can be carried out by the same operation as above in TFA.

The obtained crude peptide can be separated and purified by application to HPLC. The peptide can be eluted under the optimum conditions by use of a water-acetonitrile mixed solvent conventionally used in protein purification. A fraction corresponding to a peak in the obtained profile of chromatography is separated and then freeze-dried. The peptide fraction thus purified is identified by, for example, mass spectrometric molecular weight analysis, amino acid composition analysis, or amino acid sequence analysis.

The present invention also relates to an agent for treating multiple sclerosis in which plasmablasts occur at high levels and in which the indicator of change in immature plasmablasts is high, the agent comprising an IL-6 inhibitor as an active ingredient. The "relapsing-remitting multiple sclerosis in which plasmablasts occur at high levels and in which the indicator of change in immature plasmablasts is high" according to the present invention refers to multiple sclerosis with a high amount of plasmablasts (PBs), which has been determined to show an increase in the amount of immature plasmablasts (PBs) after administration of an IL-6 inhibitor as compared to before the administration, or in which the amount of increase in immature plasmablasts (PBs) due to administration of an IL-6 inhibitor is large. Alternatively, it refers to multiple sclerosis in which the amount of plasmablasts (PBs) is high and the amount of follicular helper T cells is low.

In the present invention, "relapsing-remitting multiple sclerosis in which plasmablasts occur at high levels and in which the indicator of change in immature plasmablasts is high" can also be rephrased as "relapsing-remitting multiple sclerosis in which plasmablasts occur at high levels and in which follicular helper T cells occur at low levels".

In the present invention, the phrase "comprising as an active ingredient" means comprising an IL-6 inhibitor as at least one of the active ingredients and does not limit the content percentage thereof. The therapeutic agent of the present invention may also contain active ingredients other than the IL-6 inhibitor. The therapeutic agent of the present invention may be used not only for therapeutic purposes but for preventive purposes.

The therapeutic agent of the present invention can be formulated according to a routine method (e.g., Remington's Pharmaceutical Science, latest edition, Mark Publishing Company, Easton, U.S.A). The therapeutic agent of the present invention may contain a pharmaceutically acceptable carrier and/or additive according to needs. The therapeutic agent of the present invention can contain, for example, a surfactant (PEG, Tween, etc.), an excipient, an antioxidant (ascorbic acid, etc.), a colorant, a flavoring agent, a preservative, a stabilizer, a buffer (phosphate, citrate, other organic acids, etc.), a chelating agent (EDTA, etc.), a suspending agent, a tonicity agent, a binder, a disintegrant, a lubricant, a flowability enhancer, and a corrigent. However, the therapeutic agent of the present invention may appropriately contain, without being limited to the above agents, other carriers routinely used. Specific examples thereof can include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium-chain fatty acid triglyceride, polyoxyethylene hydrogenated castor oil 60, white soft sugar, carboxymethylcellulose, corn starch, and inorganic salts. Also, the therapeutic agent of the present invention may contain other low-molecular-weight polypeptides, proteins (e.g., serum albumin, gelatin, and immunoglobulin), and amino acids. In the case of preparing an aqueous solution for injection, the IL-6 inhibitor is dissolved in, for example, an isotonic solution containing saline, glucose, or other adjuvants. Examples of the adjuvants include D-sorbitol, D-mannose, D-mannitol, and sodium chloride. The solution may be further used in combination with an appropriate solubilizer, for example, an alcohol (ethanol, etc.), a polyalcohol (propylene glycol, PEG, etc.), or a nonionic surfactant (polysorbate 80 or HCO-50).

The IL-6 inhibitor may be enclosed in a microcapsule (microcapsule made of hydroxymethylcellulose, gelatin, poly[methyl methacrylate], or the like) or prepared into a colloid drug delivery system (liposomes, albumin microspheres, microemulsions, nanoparticles, and nanocapsules, etc.) (see e.g., Remington's Pharmaceutical Science 16th edition & Oslo Ed. (1980)). Methods for formulating drugs as sustained-release drugs are also known in the art and may be applied to the IL-6 inhibitor of the present invention (Langer et al., J. Biomed. Mater. Res. (1981) 15: 167-277; Langer, Chem. Tech. (1982) 12: 98-105; U.S. Pat. No. 3,773,919; EP 58,481; Sidman et al., Biopolymers (1983) 22: 547-56; and EP 133,988). In addition, the therapeutic agent of the present invention may be supplemented or mixed with hyaluronidase to allow an increased amount of fluid to be subcutaneously administered (e.g., WO2004/078140).

The therapeutic agent of the present invention can be administered through any of oral and parenteral routes and is preferably administered parenterally. Specifically, the therapeutic agent of the present invention is administered to a patient through injection or percutaneous administration. Examples of the dosage form of the injection include systemic or local administration by intravenous injection, intramuscular injection, intraperitoneal injection, subcutaneous injection, or such. The therapeutic agent of the present invention may be injected locally, particularly, intramuscularly, to a treatment site or the neighborhood thereof. Examples of the dosage form of the percutaneous administration include ointments, gels, creams, poultices, and patches, which permit systemic or local administration. The administration method can be appropriately selected according to the age and symptoms of a patient. The dose can be selected, for example, within the range of 0.0001 mg to 100 mg of the active ingredient per kg of body weight per dose. Alternatively, for example, when administering to a human patient, the range of 0.001 to 1000 mg/kg body weight of the active ingredient per patient can be selected. The single dose preferably contains, for example, approximately 0.01 to 50 mg/kg body weight of the antibody of the present invention. However, the therapeutic agent of the present invention is not limited by these doses.

The therapeutic agent of the present invention can be used alone for treating multiple sclerosis in a human or an animal, in which plasmablasts occur at high levels and the indicator of change in immature plasmablasts is high. Alternatively, the therapeutic agent of the present invention may be orally administered as a mixture with other ingredients that may be commonly used in pharmaceuticals or foods. The therapeutic agent of the present invention can also be used in combination with other compounds, microbes, or the like known to have a therapeutic and/or preventive effect on multiple sclerosis.

The present invention further relates to a method for treating multiple sclerosis in which plasmablasts occur at high levels and the indicator of change in immature plasmablasts is high, which comprises the step of administering an IL-6 inhibitor to an animal. Examples of the subject to which the IL-6 inhibitor is administered include mammals. Examples of the mammals include humans and non-human mammals in need of the treatment or prevention of relapsing-remitting multiple sclerosis and preferably include humans and monkeys, and more preferably humans.

The present invention further relates to an IL-6 inhibitor for use in treating multiple sclerosis in which plasmablasts occur at high levels and in which the indicator of change in immature plasmablasts is high. Alternatively, the present invention relates to the use of an IL-6 inhibitor in the production of an agent for treating multiple sclerosis in which plasmablasts occur at high levels and in which the indicator of change in immature plasmablasts is high.

The present invention further relates to a method for producing an agent for treating multiple sclerosis in which plasmablasts occur at high levels and in which the indicator of change in immature plasmablasts is high, which comprises the step of mixing an IL-6 inhibitor with a pharmaceutically acceptable carrier.

All prior art documents cited herein are incorporated herein by reference.

EXAMPLES

Next, the present invention will be explained more specifically with reference to the Examples. However, the present invention is not to be construed as being limited to the following Examples.

An objective of multiple sclerosis (MS) treatment is to decrease the number of relapses and improve the clinical symptoms. Accordingly, the number of relapses during twelve months before and after introduction of an IL-6 inhibitor, tocilizumab (TCZ), were compared. Clinical symptoms were compared based on the following indicators obtained before introduction of TCZ and twelve months after introduction of TCZ. Since EDSS focuses on gait disturbance, NRS and ophthalmologic evaluations were used in combination.

Figure 2:
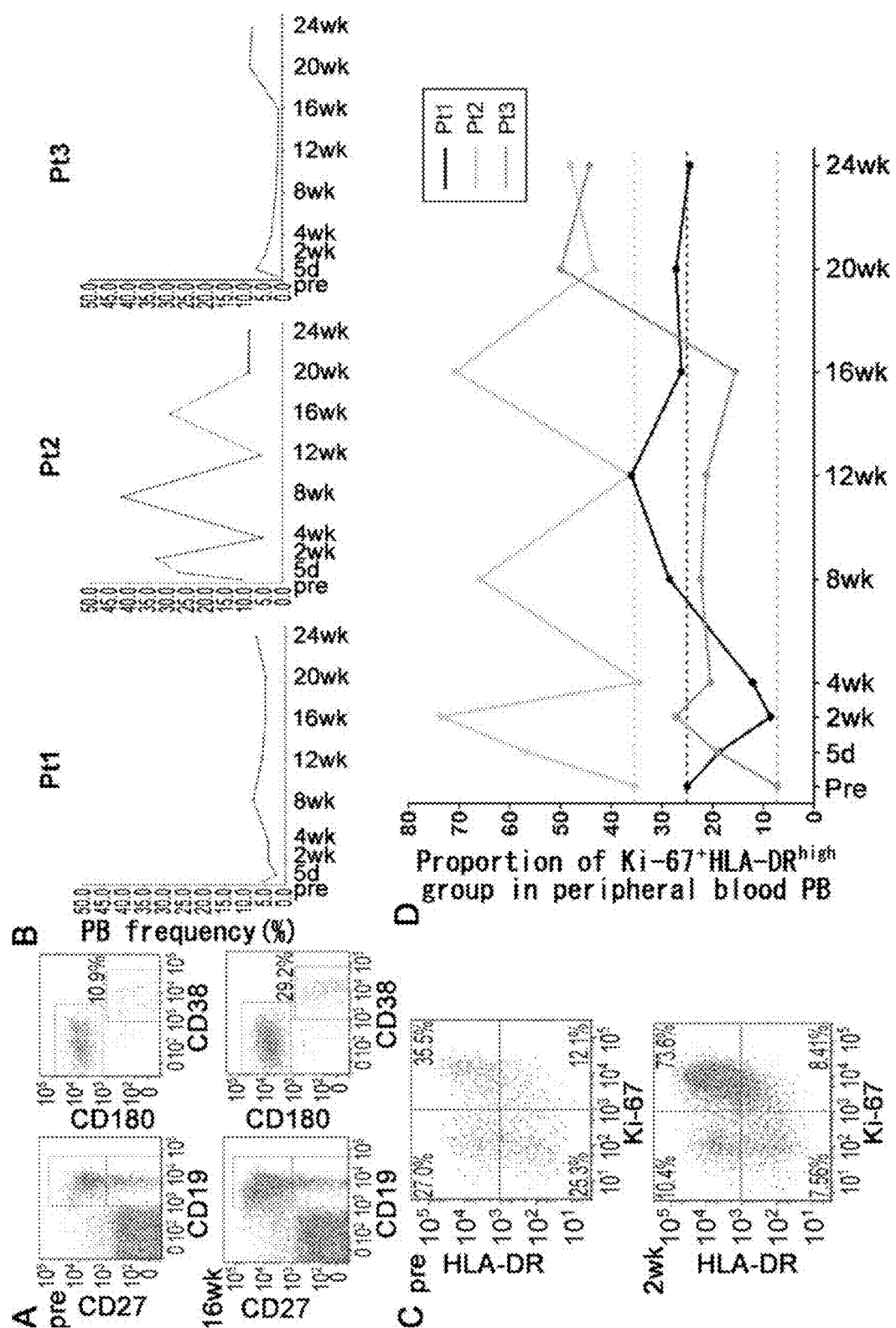
FIG. 2 shows changes in peripheral blood PBs associated with tocilizumab administration in RRMS patients having a high peripheral blood PB frequency. Tocilizumab (TCZ) was administered to three RRMS patients having a high peripheral blood PB frequency (Pt1, Pt2, and Pt3; Pt1 belonged to the $T_{FH}$-high, and Pt2 and Pt3 belonged to the $T_{FH}$-low group) for six months, and the peripheral blood PB frequency and expression of Ki-67 and HLA-DR in peripheral blood PBs were measured by flow cytometry. Since the expression of the cell proliferation marker Ki-67 and the MHC class II molecule HLA-DR decreases as PB differentiation progresses (Jourdan, M. et al. An in vitro model of differentiation of memory B cells into plasmablasts and plasma cells including detailed phenotypic and molecular characterization. Blood 2009, 114:5173-5181; and Cocco, M. et al. In vitro generation of long-lived human plasma cells. J. Immunol. 2002, 189:5773-5785), the expression levels of these molecules in PBs reflect the degree of PB differentiation. The peripheral blood PB frequency is defined as the proportion (%) of PBs among peripheral blood CD19-positive B cells. A) shows the peripheral blood PB frequencies in Pt2 before TCZ administration (pre) and 16 weeks after TCZ administration (16 wk). For PBMCs, CD19-positive-CD27-positive cells were fractionated from CD19-positive B cells (plots in the left column). This fraction was further plotted with respect to the expression of CD180 and CD38, and CD19+CD27+CD180−CD38$^{high}$ cells were defined as PBs (plots in the right column; the lower right fraction indicates PBs). The numbers in the plot represent the PB frequencies. B) shows the change in peripheral blood PB frequencies over time in three cases of TCZ administration. None of the three cases show a decrease in PBs due to TCZ administration. pre: before administration. 5d: five days after administration. wk: week (2 wk means two weeks after administration). C) shows the expression of Ki-67 and HLA-DR in Pt2 peripheral blood PBs. The division lines in the plot separate between the Ki-67-positive group and the Ki-67-negative group, or the HLA-DR high-expression (high) group and the HLA-DR low-expression (low) group. The numbers in the plot show the percentages of the respective fractions. At two weeks after the administration (2 wk), when compared to before TCZ administration (pre), the proportion of the Ki-67+HLA-DR$^{high}$ group, which is at a low differentiation stage and immature, increased from 35.5% to 73.6%. D) shows the time course of the proportion of the Ki-67+HLA-DR$^{high}$ group among peripheral blood PBs in the three cases of TCZ administration. The dashed lines indicate the measured values before the administration in each case. The relative increase of the group was striking in Pt2 and Pt3, whereas it remained slight in Pt1. When B cells differentiate into PBs, they functionally mature after completing proliferation. Since IL-6 promotes this maturation and not the proliferation, the increase of immature PBs in Pt2 and Pt3 does not contradict the effects of IL-6 inhibition (Jourdan, M. et al. and Cocco, M. et al.). Labeling of the horizontal axis conforms to B.
Figure 3:
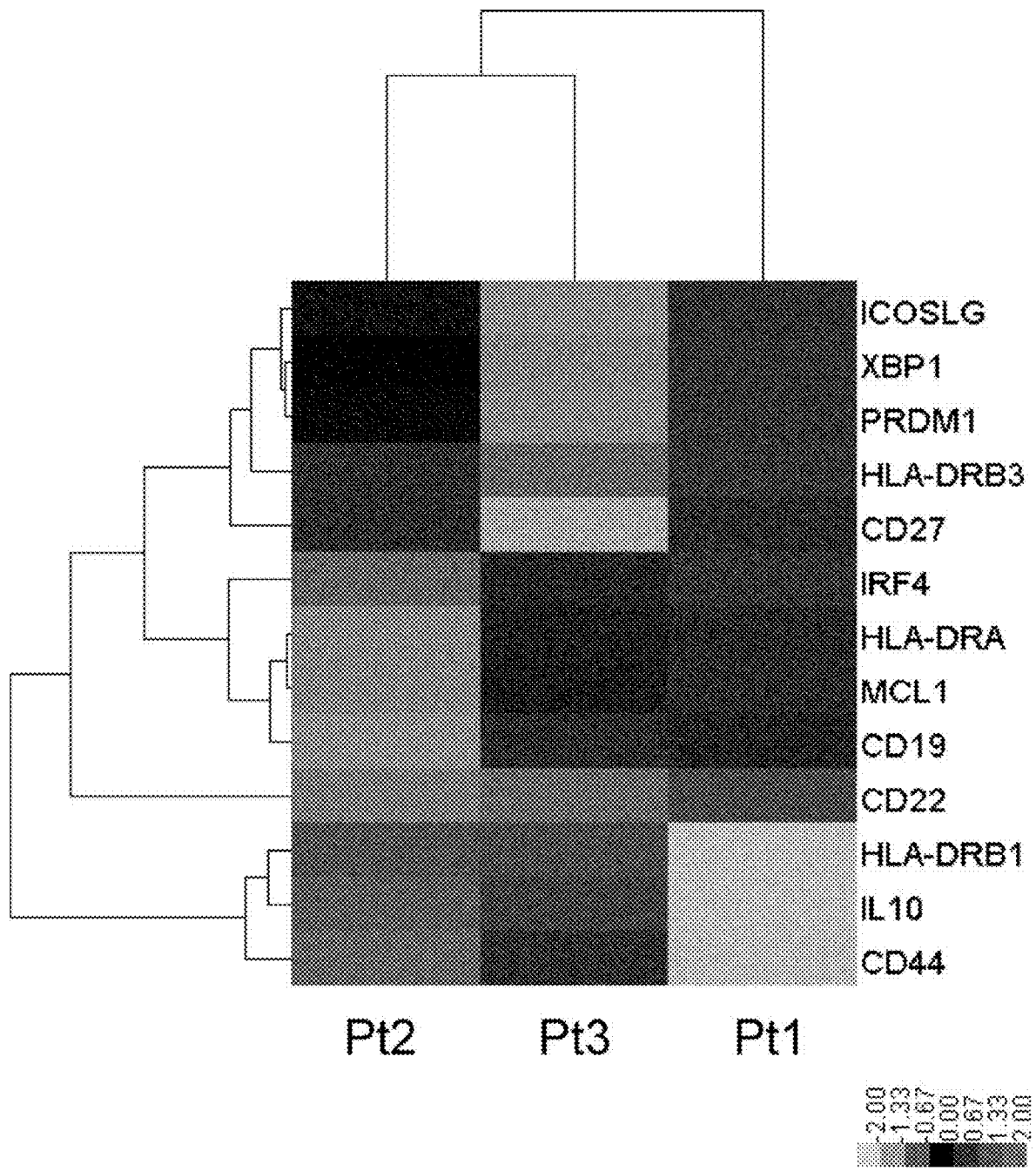
FIG. 3 shows comparison of gene expression in peripheral blood PBs derived from RRMS patients having a high peripheral blood PB frequency to whom tocilizumab was administered. From the peripheral blood of three MS patients having a high peripheral blood PB frequency to whom tocilizumab (TCZ) was administered, PBs were separated and collected by flow cytometry, and the gene expression in the PBs was profiled using nCounter (registered trademark) (NanoString Technologies). Of the profiled genes, 13 genes relating to the differentiation and function of PB were selected, their normalized expression levels in each case were converted to z scores, and the scores were compared using a heatmap. A two-way hierarchical clustering was also performed to show homology of the cases (written below the heatmap) in terms of their gene expression patterns, and homology of the genes (names of the genes are written on the left side of the heatmap) in terms of their expression patterns among the cases, by using dendrograms. These analyses were performed using the software nSolver ver. 2.0 (registered trademark) provided by NanoString Technologies. While the expression levels of transcription factors Blimp-1 (PRDM1), IRF-4 (IRF4), and Xbp-1 (XBP1) correlate with the degree of promotion of PB differentiation (Jourdan, M. et al., and Cocco, M. et al.), their expression levels were highest in Pt1. This does not contradict the fact that the increase of peripheral blood Ki-67$^+$ HLA-DR$^{high}$ immature PBs associated with TCZ administration is slight in Pt1 while it is high in Pt2 and Pt3. As far as the function of PBs is concerned, PBs derived from Pt2 and Pt3 show remarkably enhanced expression of regulatory cytokine IL-10. They are also characterized by a high expression level of cell adhesion factor CD44. It has recently been reported that, in MS model experimental autoimmune encephalomyelitis (EAE) induced by MOG$_{35-55}$, immature PBs highly expressing CD44 that have differentiated in a regional lymph node suppress the pathological conditions via IL-10 production (Matsumoto, M. et al. Interleukin-10-producing plasmablasts exert regulatory function in autoimmune inflammation. Immunity 2014, 41:1040-1051). This suggests that immature PBs induced by TCZ administration may also suppress pathological conditions of MS in a similar manner. In fact, Pt2 and Pt3 were cases of complete response to TCZ. In view of the above, the high efficacy observed in the $T_{FH}$-low group, which is presumed to have pathological conditions closer to neuromyelitis optica than the other RRMS patients with a high peripheral blood PB frequency, is considered reasonable because TCZ shows remarkable effects on pathological conditions of neuromyelitis optica (Araki, M., Matsuoka, T., Miyamoto, K., Kusunoki, S., Okamoto, T., Murata, M., Miyake, S., Aranami, T., and Yamamura, T. Efficacy of the anti-IL-6 receptor antibody tocilizumab in neuromyelitis optica: a pilot study. Neurology 2014, 82:1302-1306).

MS disability status scale, Expanded Disability Status Scale (EDSS)
Numerical Rating Scale (NRS) relating to malaise and neuralgia of the limbs and trunk
Ophthalmologic evaluations such as vision test and visual field test As indicated below, the subjects were three groups of PB-high MS patients (Pt1, Pt2, and Pt3) having high peripheral blood PB frequencies (FIGS. 1 and 2).

Pt1: $T_{FH}$-high group showing a high frequency of peripheral blood follicular helper T cells
Pt2 and Pt3: $T_{FH}$-low group showing a low frequency of peripheral blood follicular helper T cells In Pt2, four relapses accompanying worsening of gait disturbance were observed during the twelve months before TCZ introduction; however, no significant relapse was observed twelve months after the introduction, and this did not accompany worsening of EDSS. NRS relating to malaise and neuralgia both improved from 6 to 4. In Pt3, constriction of both visual fields was initially present, and one instance of relapse due to progression of right visual field constriction was observed during the twelve months before TCZ introduction; however, no relapse took place after the introduction, and remarkable improvement of both visual fields was also observed. EDSS also improved from 4.0 to 3.5. On the other hand, in Pt1, there was no relapse during the nine months after TCZ introduction; however, since two relapses took place at ten and eleven months after the introduction and EDSS worsened from 4.0 to 5.0, the administration was discontinued. From these results, it was determined that TCZ is effective in Pt2 and Pt3, but not sufficiently effective in Pt1.

In Pt2 and Pt3, which progressed favorably under treatment with tocilizumab administration, the amount of peripheral blood PBs had been found to be high before tocilizumab administration as shown in FIG. 2. Therefore, the therapeutic effect of an IL-6 inhibitor on relapsing-remitting multiple sclerosis (RRMS) was found to be predictable using the amount of peripheral blood PBs as an indicator. Furthermore, in contrast to Pt1 where treatment was ineffective, the amount of peripheral blood follicular helper T ($T_1$) cells was small in Pt2 and Pt3. Therefore, in relapsing-remitting multiple sclerosis in which the amount of peripheral blood PBs is high, it was found that the amount of peripheral blood T cells can serve as an indicator for predicting the therapeutic effect on RRMS.

Plasmablasts (PBs) differentiate from naive or memory B cells in a secondary lymphoid tissue, and contribute to the body's defense through antibody production during infection and such. When naive B cells are activated by being subjected to antigen stimulation, they interact with CD4-positive T cells and a portion of them quickly differentiate into immature PBs, and make initial responses to antigens such as the source of infection. Meanwhile, the remaining activated naive B cells serve as germinal center B cells and form a germinal center, and in this structure, they are determined to differentiate into PBs through interaction with follicular helper T cells (Craft, J. E. Nat. Rev. Rheumatol. 2012; 8: 360-2; and Crotty, S. Immunity 2014; 41: 529-42). Immature PBs produced in this process mature through repeated interaction with follicular helper T cells, and exert strong function in antigen removal (Liu, D., et al. Nature 2015; 517: 214-8). The interaction between germinal center B cells and follicular helper T cells produce memory B cells at the same time. Memory B cells continue to exist even after an immunological event such as an infection has settled, and have the ability to differentiate into more mature PBs, more quickly than naive B cells subjected to the same specific antigen stimulation (Craft, J. E. and Crotty, S.). It has recently been reported that memory B cells differentiating into PBs also show interaction with follicular helper T cells waiting near a disappearing germinal center, suggesting that follicular helper T cells also play an important role in generation of mature PBs from these memory B cells (Aiba, Y, et al. Proc Natl Acad Sci USA 2010; 107: 12192-7).

Recently, in mice, follicular helper T cells circulating in the peripheral blood have been reported to exhibit high PB differentiation ability in vivo, and in humans as well, it is expected that follicular helper T cells circulate in the peripheral blood and promote PB differentiation in secondary lymphoid tissues (Sage, P. T., et al., J. Clin. Invest. 2014; 124: 5191-204). In fact, it has been shown that, in human infections and autoimmune diseases, the increase in peripheral blood follicular helper T cells correlates with the amount of specific antibodies in blood, and with clinical severity (Locci, M., et al., Immunity 2013; 39: 758-69; and Simpson, N., et al., Arthritis Rheum 2010; 62: 234-44).

INDUSTRIAL APPLICABILITY

The present invention provides a method for predicting the therapeutic effect of an IL-6 inhibitor on MS by using an indicator of change in immature plasmablasts in the peripheral blood of a multiple sclerosis patient. Furthermore, the present invention provides a novel therapeutic method for patients with multiple sclerosis in which plasmablasts occur at high levels and in which the indicator of change in immature plasmablasts is high. By the present invention, it is possible to avoid administering an IL-6 inhibitor to a patient who cannot be expected to receive the therapeutic effect of the IL-6 inhibitor or who has to suffer manifestation of serious adverse reactions or aggravation of concomitant immune disorders, and it is possible to select an appropriate treatment method.

The invention claimed is:

1. A method for treating a subject identified as having multiple sclerosis, the method comprising:
   measuring the proportion of plasmablasts in CD19+ B cells in a blood sample isolated from the subject, and determining that the proportion of plasmablasts is equal to or higher than 3.5%;
   measuring the proportion of CXCR5+CCR7+ cells in memory CD4+ T cells in a blood sample isolated from the subject, and determining that the proportion of CXCR5+CCR7+ cells is lower than 30%;
   predicting, based on both of the above determinations, that an anti-IL-6 receptor antibody is likely to be effective in treating the subject's multiple sclerosis; and
   administering the anti-IL-6 receptor antibody to the subject.

2. The method of claim 1, wherein the anti-IL-6 receptor antibody is a chimeric antibody, a humanized antibody, or a human antibody.

3. The method of claim 1, wherein the multiple sclerosis is relapsing-remitting multiple sclerosis.

4. The method of claim 1, wherein the multiple sclerosis is secondary-progressive multiple sclerosis.

5. The method of claim 1, further comprising, prior to the measuring steps, obtaining one or more peripheral blood samples from the subject.

6. The method of claim 1, wherein the proportion of CXCR5+CCR7+ cells in memory CD4+ T cells is determined to be a percent lower than 28.2%.

7. The method of claim 1, wherein the anti-IL-6 receptor antibody is tocilizumab.

8. A method for treating a subject identified as having multiple sclerosis, the method comprising:
   determining whether the proportion of plasmablasts in CD19+ B cells is equal to or higher than 3.5%, and whether the proportion of CXCR5+CCR7+ cells in memory CD4+ T cells is lower than 30% in a blood sample of the subject by:
   obtaining or having obtained one or more blood samples from the subject;
   measuring or having measured the proportion of plasmablasts in CD19+ B cells in one of the one or more blood samples; and
   measuring or having measured the proportion of CXCR5+CCR7+ cells in memory CD4+ T cells in one of the one or more blood samples; and
   if the proportion of plasmablasts in CD19+ B cells is equal to or higher than 3.5%, and the proportion of CXCR5+CCR7+ cells in memory CD4+ T cells is lower than 30% in the blood sample(s), then administering an anti-IL-6 receptor antibody to the subject,
   if the proportion of plasmablasts in CD19+ B cells is lower than 3.5%, or if the proportion of CXCR5+CCR7+ cells in memory CD4+ T cells is equal to or higher than 30% in the blood sample(s), then not administering an anti-IL-6 receptor antibody to the subject, and instead treating the subject's multiple sclerosis with another appropriate treatment.

9. The method of claim 8, wherein the multiple sclerosis is relapsing-remitting multiple sclerosis.

10. The method of claim 8, wherein the multiple sclerosis is secondary-progressive multiple sclerosis.

11. The method of claim 8, wherein the other appropriate treatment comprises administration of interferon beta.

12. The method of claim 8, wherein the anti-IL-6 receptor antibody is a chimeric antibody, a humanized antibody, or a human antibody.

13. The method of claim 8, wherein the anti-IL-6 receptor antibody is tocilizumab.

* * * * *